United States Patent
Dhawan et al.

(10) Patent No.: US 11,021,383 B2
(45) Date of Patent: Jun. 1, 2021

(54) USE OF DI-IONIC COMPOUNDS AS CORROSION INHIBITORS IN A WATER SYSTEM

(71) Applicant: ECOLAB USA INC., Saint Paul, MN (US)

(72) Inventors: Ashish Dhawan, Saint Paul, MN (US); Jeremy Moloney, Saint Paul, MN (US); Carter M. Silvernail, Saint Paul, MN (US); Boyd A. Laurent, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 16/116,413

(22) Filed: Aug. 29, 2018

(65) Prior Publication Data

US 2019/0062187 A1    Feb. 28, 2019

Related U.S. Application Data

(60) Provisional application No. 62/552,108, filed on Aug. 30, 2017.

(51) Int. Cl.
*C02F 5/12* (2006.01)
*C23F 11/14* (2006.01)
(Continued)

(52) U.S. Cl.
CPC .............. *C02F 5/12* (2013.01); *C07C 231/12* (2013.01); *C07C 237/06* (2013.01);
(Continued)

(58) Field of Classification Search
CPC ....... C02F 5/12; C07C 231/12; C07C 237/06; C07F 9/5407; C11D 1/62; C11D 3/386;
(Continued)

(56) References Cited

U.S. PATENT DOCUMENTS 4,259,217 A   3/1981  Murphy
4,355,071 A  10/1982  Chang
(Continued)

FOREIGN PATENT DOCUMENTS

BE         606234 A     7/1961
CA        1084925 A     9/1980
(Continued)

OTHER PUBLICATIONS

"Azamethonium", http://pubchem.ncbi.nlm.nih.gov/compound/9383, last modified Oct. 6, 2018 and accessed by Applicant Oct. 11, 2018.
(Continued)

*Primary Examiner* — Ellen M McAvoy
(74) *Attorney, Agent, or Firm* — McKee, Voorhees & Sease, PLC

(57) ABSTRACT

Disclosed herein are the methods of using di-cationic or di-anionic compounds, which are derived from primary amine through an aza-Michael addition with an activated olefin, in a corrosion control composition to mitigate corrosion of a surface in a water system. The disclosed methods or compositions are found to be more effective than those methods or compositions including commonly used single quaternary compounds for mitigating corrosion for a metal surface in water systems.

24 Claims, 3 Drawing Sheets

(51) Int. Cl.
  *C07F 9/54* (2006.01)
  *C11D 7/32* (2006.01)
  *C23F 11/10* (2006.01)
  *C07C 231/12* (2006.01)
  *C07C 237/06* (2006.01)
  *C11D 1/62* (2006.01)
  *C11D 3/386* (2006.01)
  *C02F 1/68* (2006.01)

(52) U.S. Cl.
  CPC .............. *C07F 9/5407* (2013.01); *C11D 1/62* (2013.01); *C11D 3/386* (2013.01); *C11D 7/3254* (2013.01); *C11D 7/3263* (2013.01); *C23F 11/10* (2013.01); *C23F 11/141* (2013.01); *C23F 11/149* (2013.01); *C02F 1/683* (2013.01); *C02F 2303/08* (2013.01); *C02F 2305/04* (2013.01)

(58) Field of Classification Search
  CPC ..... C11D 7/3263; C11D 7/3254; C23F 11/10; C23F 11/141; C23F 11/149
  See application file for complete search history.

(56) References Cited

U.S. PATENT DOCUMENTS

| | | | |
|---|---|---|---|
| 5,192,798 | A | 3/1993 | Aiken et al. |
| 5,399,746 | A | 3/1995 | Steiger et al. |
| 5,788,866 | A * | 8/1998 | Fong .................. C08G 73/0611 210/697 |
| 6,054,054 | A | 4/2000 | Robertson et al. |
| 6,797,785 | B1 | 9/2004 | Hund et al. |
| 9,164,379 | B2 | 10/2015 | Utsumi et al. |
| 2006/0008496 | A1 | 1/2006 | Kulkarni et al. |
| 2006/0289164 | A1 | 12/2006 | Smith et al. |
| 2006/0289359 | A1 | 12/2006 | Manek et al. |
| 2010/0004316 | A1 | 1/2010 | Lu et al. |
| 2012/0070341 | A1 | 3/2012 | Eder et al. |
| 2012/0115962 | A1 | 5/2012 | Lee et al. |
| 2013/0228095 | A1 * | 9/2013 | Miles .................. C09K 8/54 106/14.42 |
| 2013/0266669 | A1 | 10/2013 | Jiang et al. |
| 2013/0302736 | A1 | 11/2013 | Utsumi et al. |
| 2014/0091262 | A1 * | 4/2014 | Webber .................. C23F 11/145 252/391 |
| 2014/0124454 | A1 | 5/2014 | Nichols et al. |
| 2014/0224733 | A1 | 8/2014 | Osness et al. |
| 2015/0203738 | A1 | 7/2015 | Witham et al. |
| 2016/0010035 | A1 | 1/2016 | Liu et al. |
| 2016/0145610 | A1 | 5/2016 | Lu et al. |
| 2016/0186040 | A1 * | 6/2016 | Gill .................. C09K 8/54 |
| 2016/0264734 | A1 | 9/2016 | Boday et al. |
| 2016/0264744 | A1 | 9/2016 | Boday et al. |
| 2017/0002145 | A1 | 1/2017 | Boday et al. |
| 2017/0121560 | A1 | 5/2017 | Dockery et al. |
| 2017/0137634 | A1 * | 5/2017 | Balasubramanian .. C09D 5/086 |
| 2017/0233643 | A1 | 8/2017 | Kgashe et al. |
| 2017/0247798 | A1 * | 8/2017 | Moloney .............. C23F 11/164 |
| 2017/0349543 | A1 | 12/2017 | Siegwart et al. |
| 2017/0360040 | A1 | 12/2017 | Kost et al. |
| 2018/0105629 | A1 | 4/2018 | Tada et al. |
| 2018/0118999 | A1 | 5/2018 | Hikem et al. |
| 2018/0163020 | A1 * | 6/2018 | Zong .................. C08L 79/08 |
| 2019/0062187 | A1 | 2/2019 | Dhawan et al. |
| 2019/0223434 | A1 | 7/2019 | Balasubramanian et al. |

FOREIGN PATENT DOCUMENTS

| | | |
|---|---|---|
| CA | 2357756 A1 | 7/2000 |
| CN | 102675535 A | 9/2012 |
| CN | 103288672 A | 9/2013 |
| CN | 105523956 A | 4/2016 |
| CN | 106423269 A | 2/2017 |
| CN | 106423284 A | 2/2017 |
| CN | 106634929 A | 5/2017 |
| CN | 106946743 A | 7/2017 |
| CN | 108033895 A | 5/2018 |
| CN | 108938662 A | 12/2018 |
| DE | 1149363 B | 5/1963 |
| EP | 0327379 A2 | 8/1989 |
| EP | 0900266 B1 | 10/2002 |
| GB | 847321 | 9/1960 |
| GB | 941752 | 11/1963 |
| GB | 1550420 | 8/1979 |
| JP | 2001187751 A | 7/2001 |
| JP | 2007054710 A | 3/2007 |
| JP | 2012136504 A | 7/2012 |
| JP | 2014093768 A | 5/2014 |
| JP | 2014221859 A | 11/2014 |
| WO | 0039241 A1 | 7/2000 |
| WO | 2004056843 A2 | 7/2004 |
| WO | 2012083497 A1 | 6/2012 |
| WO | 2015084304 A1 | 6/2015 |
| WO | 2016205513 A1 | 12/2016 |
| WO | 2017003639 A2 | 1/2017 |
| WO | 2017201076 A1 | 11/2017 |
| WO | 2019046409 A1 | 3/2019 |

OTHER PUBLICATIONS

Kawakami, Jun et al., "Antibacterial Activity of Radial Compounds with Peripheral Quaternary Ammonium Units", Transactions of the Materials Research Society of Japan, 35[4]885-887, 2010.

Miller et al., "Non-viral CRISPR/Cas gene editing in vitro and in vivo enabled by synthetic nanoparticle co-delivery of Cas9 mRNA and sgRNA", Angew Chem Int Ed Engl., 56(4), pp. 1059-1063, Jan. 19, 2018.

Ning et al., "Synthesis and characterization of a novel non-polyether demulsifier", http://en.cnki.com.cn/Artcle_en/CJFDTOTAL-HXGC201301020.htm, accessed online on Aug. 28, 2018, published Jan. 2013.

Wang et al., "A novel environment-sensitive biodegradable polydisulfide with protonatable pendants for nucleic acid delivery", Journal of Controlled Release, vol. 120, pp. 250-258, May 21, 2007.

Zielinski et al., "Synteza nowych czwartorzedowych soli amoniowych do organofilizacji nanokompozytowych napelniaczy polimerowych", www.miesiecznikchemik.pl, 2007.

Fan et al., "Synthesis and Aggregation Behavior of a Hexameric Quaternary Ammonium Surfactant", Langmuir, vol. 27, pp. 10570-10579, Jul. 28, 2011.

Kawakami et al., "Antibacterial Activity of Radial Compounds with Peripheral Quaternary Ammonium Units", Transactions of the Materials Research Society of Japan, vol. 35[4], pp. 885-887, 2010.

Zhang et al., "Pamam-Based Dendrimers with Different Alkyl Chains Self-Assemble on Silica Surfaces: Controllable Layer Structure and Molecular Aggregation", J. Phys. Chem. B, vol. 122, pp. 6648-6655, Jun. 13, 2018.

Zhou et al., "Cooperative binding and self-assembling behavior of cationic low molecular-weight dendrons with RNA molecules", Organic & Biomolecular Chemistry, vol. 4, pp. 581-585, 2006.

Ecolab USA Inc, in connection with PCT/US2018/048518 filed Aug. 29, 2018, "The International Search Report and the Written Opinion of the International Searching Authority, or the Declaration", 10 pages, dated Nov. 7, 2018.

Zhang et al., "Controllable Self-Assembly of Amphiphilic Dendrimers on a Silica Surface: The Effect of Molecular Topological Structure and Salinity", Journal of Physical Chemistry, vol. 8, pp. 10990-10999, Oct. 5, 2016.

Zhang et al., "Supporting information", Beijing National Laboratory for Molecular Sciences, published with Controllable Self-Assembly of Amphiphilic Dendrimers on a Silica Surface, 4 pages, Oct. 5, 2016.

Labade et al., "Cesium fluoride catalyzed Aza-Michael addition reaction in aqueous media" Montash Chem 142, pp. 1055-1099, 5 pages, published Jul. 19, 2011.

(56) References Cited

OTHER PUBLICATIONS

International Preliminary Examining Authority in connection with PCT/US2019/048441 filed Aug. 28, 2019, "Written Opinion of the International Preliminary Examining Authority", 7 pages, dated Jul. 15, 2020.
Somerscales, Euan F.C., "Fundamentals of Corrosion Fouling", Experimental Thermal and Fluid Science, vol. 14, pp. 335-355, 1997.
Zielinksi, Wojciech et al., "TI-Synthesis of new quaternary ammonium salts for organophilization of fillers for Polymeric nanocomposites", D1: Database Chemical Abstracts [Online] chemical abstracts; XP55789968, Database accession No. 2007:1236240, 2 pages, Jan. 1, 2007.

* cited by examiner

USE OF DI-IONIC COMPOUNDS AS CORROSION INHIBITORS IN A WATER SYSTEM

CROSS-REFERENCE TO RELATED APPLICATIONS

This application claims priority and relates to U.S. Provisional Application Ser. No. 62/552,108, filed on Aug. 30, 2017 and entitled "MOLECULES HAVING ONE HYDROPHOBIC AND TWO IDENTICAL HYDROPHILIC GROUPS AND COMPOSITIONS THEREOF AND METHODS OF PREPARATION THEREOF." The entire contents of this patent application are hereby expressly incorporated herein by reference including, without limitation, the specification, claims, and abstract, as well as any figures, tables, or drawings thereof.

This application also relates to U.S. non-Provisional application Ser. No. 16/116,222, filed on Aug. 29, 2018 and titled "MOLECULES HAVING ONE HYDROPHOBIC GROUP AND TWO IDENTICAL HYDROPHILIC IONIC GROUPS AND COMPOSITIONS THEREOF AND METHODS OF PREPARATION THEREOF." The entire contents of this patent application are hereby expressly incorporated herein by reference including, without limitation, the specification, claims, and abstract, as well as any figures, tables, or drawings thereof.

FIELD OF THE INVENTION

The present disclosure relates generally to the field of corrosion control in a water system. In particular, the present disclosure relates to using a new class of compounds that comprise two identical hydrophilic ionic groups and one hydrophobic group for inhibiting corrosion in a water system. The compounds disclosed herein share some structural features with conventional or Gemini surfactants but are structurally distinguishable from the existing surfactants. The compounds disclosed herein are found to be effective corrosion inhibitors.

BACKGROUND OF THE INVENTION

Quaternary ammonium compounds comprise an important subcategory of surfactants because they contain unique properties. A main distinction between quaternary ammonium compounds and other surfactants is their unique structure. Quaternary ammonium compounds consist mainly of two moieties, a hydrophobic group, e.g., long alkyl group, and a quaternary ammonium salt group. The unique positive charge of the ammonium plays a key role, e.g., electrostatic interactions, between the surfactant and surface.

Industrial water systems employ process water to serve many different purposes but may be prone to microbial contamination and fouling. Metal surfaces in any water system are prone to corrosion, partly due to microbial contamination and fouling.

Corrosion inhibitors are often added into a water system to protect its metal surfaces infrastructure, such as carbon steel pipelines, from corrosion. However, the quaternary ammonium compounds used for such purposes are often bis quaternary species or species quaternized with benzyl chloride and are known to be very hazardous. In addition, governmental regulations exist to release any water containing single quaternary compounds into the environment.

Therefore, there is a continuing need for different or alternative quaternary ammonium compounds that are better and safer corrosion control agents.

Accordingly, it is an objective of the present disclosure to develop novel corrosion control agents having improved corrosion control properties.

It is a further objective of the disclosure to develop methods and corrosion control compositions to make the corrosion in a water system more efficient and effective.

These and other objects, advantages and features of the present disclosure will become apparent from the following specification taken in conjunction with the claims set forth herein.

BRIEF SUMMARY OF THE INVENTION

Disclosed herein are the methods and compositions for corrosion control for a metal surface in a water system. Specifically, the disclosed methods and compositions for corrosion control for a water system use one or more water soluble di-cationic or di-anionic compounds derived from water soluble primary amines (Michael donor) by an aza-Michael addition reaction with an activated olefin (Michael acceptor).

The exemplary di-cationic or di-anionic compounds disclosed herein have a superior performance than the conventional single quaternary ammonium compounds used for mitigating corrosion for metal surfaces in water systems. The exemplary di-cationic or di-anionic compounds disclosed herein also show improved performance when they are used as a fouling control agent in a water system. Therefore, the disclosed corrosion control compositions or methods have an advantage of not only preventing corrosion of surfaces but also preventing microbial/biofilm growth, leading to overall reduction in chemical uses, cost, and operation complexity for operating a water system.

In one aspect, disclosed herein is a method for inhibiting corrosion at a surface in a water system, the method comprises providing a corrosion control composition or a use solution of the corrosion control composition into a water system to generate a treated water system or onto a surface of the water system, wherein the corrosion control composition comprises one or more compounds according to one of Formula I, Formula II, and Formula III and one or more additional corrosion control composition agents,

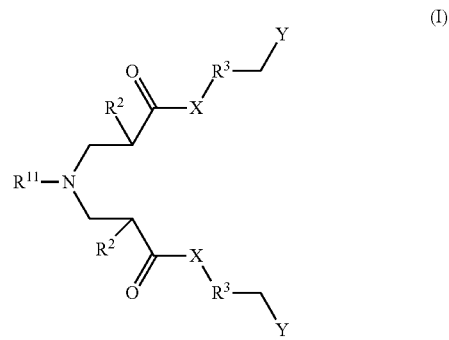

(I)

-continued

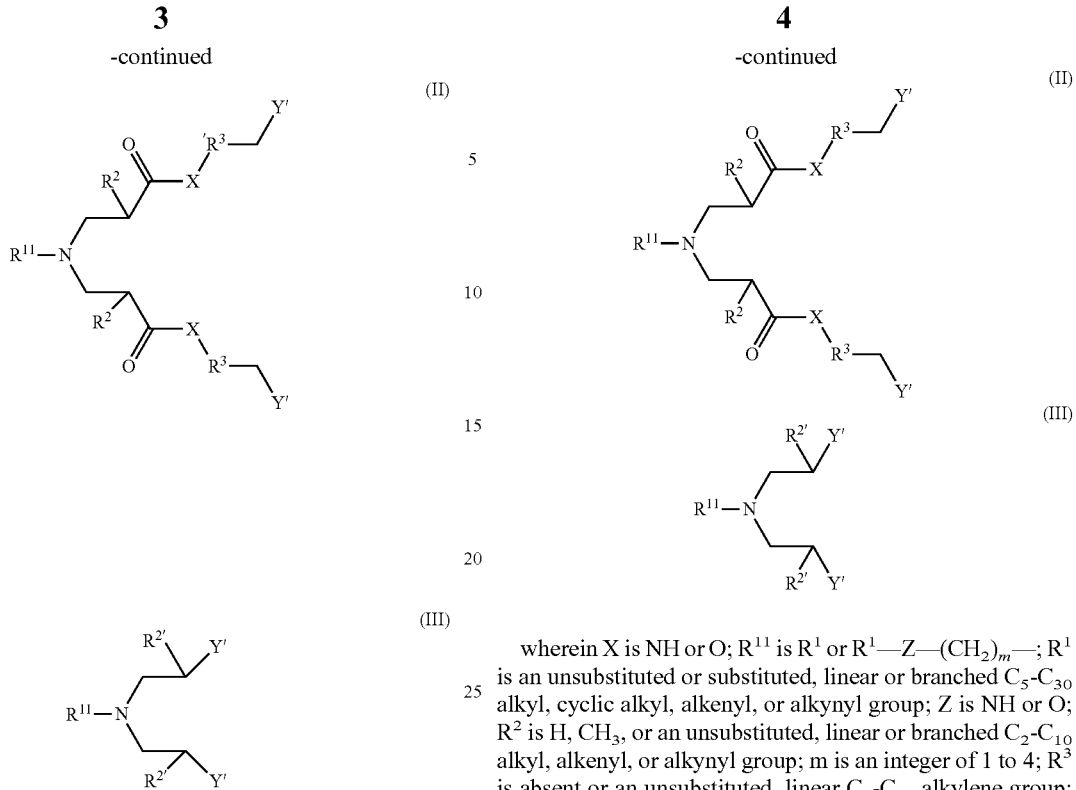

(II)

(III)

wherein X is NH or O; $R^{11}$ is $R^1$ or $R^1$—Z—$(CH_2)_m$—; $R^1$ is an unsubstituted or substituted, linear or branched $C_5$-$C_{30}$ alkyl, cyclic alkyl, alkenyl, or alkynyl group; Z is NH or O; $R^2$ is H, $CH_3$, or an unsubstituted, linear or branched $C_2$-$C_{10}$ alkyl, alkenyl, or alkynyl group; m is an integer of 1 to 4; $R^3$ is absent or an unsubstituted, linear $C_1$-$C_{30}$ alkylene group; Y is —N $R^4R^5R^{6(+)}$; Y' is —COOH, —$SO_3H$, —$PO_3H$, —$OSO_3H$, —$OPO_3H$, or a salt thereof; $R^4$, $R^5$, and $R^6$ are independently a $C_1$-$C_{10}$ alkyl group; $R^{2'}$ is H, $CH_3$, or an unsubstituted or substituted, linear or branched $C_1$-$C_{10}$ alkyl, alkenyl, alkynyl group, —COOH, —$CH_2$COOH, Y', or —$(CH_2)_m$—Y', and wherein the corrosion control composition mitigates corrosion on the surface in the water system.

In other aspect, disclosed herein is a corrosion control composition, the corrosion control composition comprises one or more compounds according to one of Formula I, Formula II, and Formula III and one or more additional corrosion control composition agents,

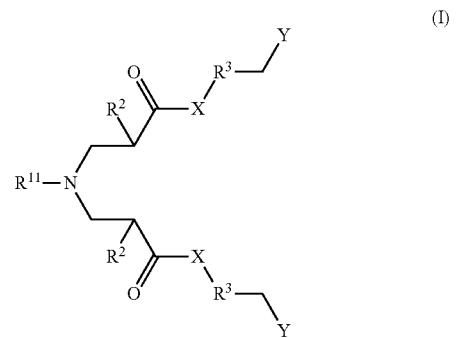

(I)

-continued (II)

(III)

wherein X is NH or O; $R^{11}$ is $R^1$ or $R^1$—Z—$(CH_2)_m$—; $R^1$ is an unsubstituted or substituted, linear or branched $C_5$-$C_{30}$ alkyl, cyclic alkyl, alkenyl, or alkynyl group; Z is NH or O; $R^2$ is H, $CH_3$, or an unsubstituted, linear or branched $C_2$-$C_{10}$ alkyl, alkenyl, or alkynyl group; m is an integer of 1 to 4; $R^3$ is absent or an unsubstituted, linear $C_1$-$C_{30}$ alkylene group; Y is —N $R^4R^5R^{6(+)}$; Y' is —COOH, —$SO_3H$, —$PO_3H$, —$OSO_3H$, —$OPO_3H$, or a salt thereof; $R^4$, $R^5$, and $R^6$ are independently a $C_1$-$C_{10}$ alkyl group; $R^{2'}$ is H, $CH_3$, or an unsubstituted or substituted, linear or branched $C_1$-$C_{10}$ alkyl, alkenyl, alkynyl group, —COOH, —$CH_2$COOH, Y', or —$(CH_2)_m$—Y', and wherein the corrosion control composition mitigates corrosion on the surface in the water system.

The forgoing summary is illustrative only and is not intended to be in any way limiting. In addition to the illustrative aspects, embodiments and features described above, further aspects, embodiments, and features of the present technology will become apparent to those skilled in the art from the following drawings and the detailed description, which shows and describes illustrative embodiments of the present technology. Accordingly, the figures and detailed description are also to be regarded as illustrative in nature and not in any way limiting.

Figure 1A:
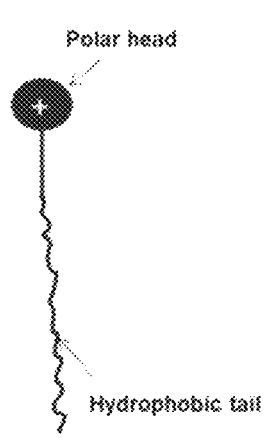
FIG. 1A, FIG. 1B, and FIG. 1C shows a representation of an exemplary compound of the disclosure (FIG. 1C), together with comparative representations for a conventional surfactant (FIG. 1A) and Gemini surfactant (FIG. 1B).

Various embodiments of the present disclosure will be described in detail with reference to the drawings, wherein like reference numerals represent like parts throughout the several views. Reference to various embodiments does not limit the scope of the disclosure. Figures represented herein are not limitations to the various embodiments according to the disclosure and are presented for exemplary illustration of the disclosure.

DETAILED DESCRIPTION OF THE PREFERRED EMBODIMENT

Disclosed herein are methods of using a new class of di-cationic or di-anionic compounds for controlling corrosion on surfaces in a water system and corresponding corrosion control compositions comprising this new class of di-cationic or di-anionic compounds. Specifically, using one or more di-cationic or di-anionic compounds, which comprise two identical hydrophilic groups and one hydrophobic group and are derived from an aza-Michael addition reaction between a primary amine (Michael donor) and activated olefin (Michael acceptor), as corrosion control agents are disclosed.

The embodiments of this disclosure are not limited to particular compositions and methods of use which can vary and are understood by skilled artisans. It is further to be understood that all terminology used herein is for describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this disclosure are presented in a range format. The description in range format is merely for convenience and brevity and should not be construed as an inflexible limitation on the scope of the disclosure. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring and liquid handling procedures used for making concentrates or use solutions in the real world; through error in these procedures; through differences in the manufacture, source, or purity of the ingredients used to make the compositions or carry out the methods; and the like. The term "about" also encompasses amounts that differ due to novel equilibrium conditions for a composition resulting from a particular initial mixture. Whether or not modified by the term "about", the claims include equivalents to the quantities.

As used herein, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, or 6 substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having two to about 30 carbon atoms, and further including at least one double bond. In some embodiments, an alkenyl group has from 2 to about carbon, or typically, from 2 to 10 carbon atoms. Alkenyl groups may be substituted or unsubstituted. For a double bond in an alkenyl group, the configuration for the double bond can be a trans or cis configuration. Alkenyl groups may be substituted similarly to alkyl groups.

Alkynyl groups are straight chain, branched, or cyclic alkyl groups having two to about 30 carbon atoms, and further including at least one triple bond. In some embodiments, an alkynyl group has from 2 to about carbon, or typically, from 2 to 10 carbon atoms. Alkynyl groups may be substituted or unsubstituted. Alkynyl groups may be substituted similarly to alkyl or alkenyl groups.

As used herein, the terms "alkylene", "cycloalkylene", alkynylides, and alkenylene", alone or as part of another substituent, refer to a divalent radical derived from an alkyl, cycloalkyl, or alkenyl group, respectively, as exemplified by —$CH_2CH_2CH_2$—. For alkylene, cycloalkylene, alkynylene, and alkenylene groups, no orientation of the linking group is implied.

The term "ester" as used herein refers to —$R^{30}COOR^{31}$ group. $R^{30}$ is absent, a substituted or unsubstituted alkylene, cycloalkylene, alkenylene, alkynylene, arylene, aralkylene, heterocyclylalkylene, or heterocyclylene group as defined herein. $R^{31}$ is a substituted or unsubstituted alkyl, cycloalkyl, alkenyl, alkynyl, aryl, aralkyl, heterocyclylalkyl, or heterocyclyl group as defined herein.

The term "amine" (or "amino") as used herein refers to —$R^{32}NR^{33}R^{34}$ groups. $R^{32}$ is absent, a substituted or unsubstituted alkylene, cycloalkylene, alkenylene, alkynylene, arylene, aralkylene, heterocyclylalkylene, or heterocyclylene group as defined herein. $R^{33}$ and $R^{34}$ are independently hydrogen, or a substituted or unsubstituted alkyl, cycloalkyl, alkenyl, alkynyl, aryl, aralkyl, heterocyclylalkyl, or heterocyclyl group as defined herein.

The term "amine" as used herein also refers to an independent compound. When an amine is a compound, it can be represented by a formula of $R^{32'}NR^{33'}R^{34'}$ groups, wherein $R^{32'}$, $R^{33'}$, and $R^{34'}$ are independently hydrogen, or a substituted or unsubstituted alkyl, cycloalkyl, alkenyl, alkynyl, aryl, aralkyl, heterocyclylalkyl, or heterocyclyl group as defined herein.

The term "alcohol" as used herein refers to —$R^{35}OH$ groups. $R^{35}$ is absent, a substituted or unsubstituted alkylene, cycloalkylene, alkenylene, alkynylene, arylene, aralkylene, heterocyclylalkylene, or heterocyclylene group as defined herein.

The term "carboxylic acid" as used herein refers to —$R^{36}COOH$ groups. $R^{36}$ is absent, a substituted or unsubstituted alkylene, cycloalkylene, alkenylene, alkynylene, arylene, aralkylene, heterocyclylalkylene, or heterocyclylene group as defined herein.

The term "ether" as used herein refers to —$R^{37}OR^{38}$ groups. $R^{37}$ is absent, a substituted or unsubstituted alkylene, cycloalkylene, alkenylene, alkynylene, arylene, aralkylene, heterocyclylalkylene, or heterocyclylene group as defined herein. $R^{38}$ is a substituted or unsubstituted alkyl, cycloalkyl, alkenyl, alkynyl, aryl, aralkyl, heterocyclylalkyl, or heterocyclyl group as defined herein.

The term "solvent" as used herein refers to any inorganic or organic solvent. Solvents are useful in the disclosed method or article, product, or composition as reaction solvent or carrier solvent. Suitable solvents include, but are not limited to, oxygenated solvents such as lower alkanols, lower alkyl ethers, glycols, aryl glycol ethers and lower alkyl glycol ethers. Examples of other solvents include, but are not limited to, methanol, ethanol, propanol, isopropanol and butanol, isobutanol, ethylene glycol, diethylene glycol, triethylene glycol, propylene glycol, dipropylene glycol, mixed ethylene-propylene glycol ethers, ethylene glycol phenyl ether, and propylene glycol phenyl ether. Water is a solvent too. The solvent used herein can be of a single solvent or a mixture of many different solvents.

Glycol ethers include, but are not limited to, diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether, propylene glycol phenyl ether, and the like, or mixtures thereof.

Di-Cationic or Di-Anionic Compounds Derived from an Aza-Michael Addition Reaction Between a Primary Amine and an Activated Olefin The di-cationic or di-anionic compounds disclosed herein are derived from an aza-Michael Addition Reaction between a primary amine (Michael donor) and an activated olefin (Michael acceptor) containing a hydrophilic ionic group at a temperature of from about −20° C. to about 200° C., in some embodiments, for from about 10 minutes to about 48 hours.

An aliphatic amine group may undergo an aza-Michael Addition reaction when in contact with an unsaturated hydrocarbon moiety (e.g., carbon-carbon double bond) that is in proximity of an electron withdrawing group such as carbonyl, cyano, or nitro group. Specifically, the Michael addition is a reaction between nucleophiles and activated olefin and alkyne functionalities, wherein the nucleophile adds across a carbon-carbon multiple bond that is adjacent to an electron withdrawing and resonance stabilizing activating group, such as a carbonyl group. The Michael addition nucleophile is known as the "Michael donor", the activated electrophilic olefin is known as the "Michael acceptor", and reaction product of the two components is known as the "Michael adduct." Examples of Michael donors include, but are not restricted to, amines, thiols, phosphines, carbanions, and alkoxides. Examples of Michael acceptors include, but are not restricted to, acrylate esters, alkyl methacrylates, acrylonitrile, acrylamides, maleimides, cyanoacrylates and vinyl sulfones, vinyl ketones, nitro ethylenes, α, β-unsaturated aldehydes, vinyl phosphonates, acrylonitrile, vinyl pyridines, azo compounds, beta-keto acetylenes and acetylene esters.

As used herein, an "activated olefin" refers to a substituted alkene in which at least one of the double-bond carbon has a conjugated electron withdrawing group. Examples of activated olefins include, but not limited to, α, β-unsaturated carbonyl compounds (such as $CH_2$=$CHCO$—$NH$—$CH_3$, alkyl-$CH$=$CH$—$CO$-alkyl, $CH_2$=$CH_2C(O)$—$O$—$CH_3$), $CH_2$=$CH$—$COOH$, $CH_2$=$CH(CH_3)$—$COOH$, $CH_2$=$CH$—$SO_3H$, and like.

It was found that the Aza-Michael addition can be used to synthesize the disclosed di-cationic or di-anionic compounds under mild conditions and with a high yield for the compounds used in the disclosed methods or compositions herein in a reasonable reaction time as descripted above.

Aza-Michael addition reaction can be catalyzed by a strong acid or base. In some cases, some ionic liquids can function both as reaction media and catalyst. The preferred catalyst for the Aza-Michael addition reaction to synthesize the disclosed compounds is a base. Exemplary base catalyst can be hydroxide and amines. If the reaction to synthesize the disclosed compounds includes a primary amine or a molecule having a prime amine group, the primary amine or the molecule itself can function as a catalyst for the reaction. In such embodiments, no additional catalyst is necessary, or an additional catalyst is optional. Other preferred catalysts include amidine and guanidine bases.

The use of solvent and/or diluent for the reaction is optional. When employed, a wide range of non-acidic solvents are suitable, such as, for example, water, ethers (e.g., tetrahydrofuran (THF)), aromatic hydrocarbons (e.g., toluene and xylene), alcohols (e.g., n-butanol), esters (e.g., ethyl 3-ethoxypropionate), and the like. A wide range of solvents can be used for the reaction because the synthesis process is relatively insensitive to solvent. When solvent (or diluent) is employed, loading levels can range from as low as about 10 wt-% up to about 80 wt-% and higher. The solvent loading level can be about 0 wt-%, from about 1 wt-% to about 10 wt-%, from about 10 wt-% to about 20 wt-%, from about 20 wt-% to about 30 wt-%, from about 30 wt-% to about 40 wt-%, from about 40 wt-% to about 50 wt-%, from about 50 wt-% to about 60 wt-%, from about 60 wt-% to about 70 wt-%, from about 70 wt-% to about 80 wt-%, from about 1 wt-% to about 20 wt-%, from about 20 wt-% to about 40 wt-%, from about 40 wt-% to about 60 wt-%, from about 60 wt-% to about 80 wt-%, from about 40 wt-% to about 70 wt-%, about 5 wt-%, about 15 wt-%, about 25 wt-%, about 35 wt-%, about 45 wt-%, about 55 wt-%, about 65 wt-%, about 75 wt-%, or any value there between of the final reaction mixture.

Generally, the reaction can be carried out at a temperature over a wide range of temperatures. The reaction temperature can range from about −20° C. to about 200° C., from about 0° C. to about 150° C., more preferably from about 50° C. to about 80° C. The contacting temperature can be from about 10° C. to about 140° C., about 20° C. to about 130° C., about 30° C. to about 120° C., about 40° C. to about 110° C., about 50° C. to about 100° C., about 60° C. to about 90° C., about 70° C. to about 80° C., about 0° C. to about 20° C., about 20° C. to about 40° C., about 40° C. to about 60° C., about 60° C. to about 80° C., about 80° C. to about 100° C., about 100° C. to about 120° C., about 120° C. to about 150° C., about 5° C., about 25° C., about 45° C., about 65° C., about 85° C., about 105° C., about 125° C., about 145° C., or any value there between. The reaction temperature can be about the same from starting of the reaction to end of the reaction and can be changed from one temperature to another while the reaction is going on.

The reaction time for the synthesis of the compounds disclosed herein can vary widely, depending on such factors as the reaction temperature, the efficacy and amount of the catalyst, the presence or absence of diluent (solvent), and the like. The preferred reaction time can be from about 10 minutes to about 48 hours, from about 0.5 hours to about 48 hours, from about 1 hour to 40 hours, from about 2 hours to 38 hours, from about 4 hours to about 36 hours, from 6 hours to about 34 hours, from about 8 hours to about 32 hours, from about 10 hours to about 30 hours, from about 12 hours to about 28 hours, from about 14 hours to 26 hours, from about 16 hours to 24 hours, from about 18 hours to 20 hours, from about 1 hour to 8 hours, from 8 hours to 16 hours, from 8 hours to about 24 hours, about 2 hours, about 4 hours, about 6 hours, about 8 hours, about 10 hours, about 14 hours, about 16 hours, about 18 hours, about 24 hours, about 30 hours, about 36 hours, or any values there between.

The reaction for the synthesis of the compounds disclosed herein can go to completion when one mole of the primary amine or polyamine and two or more moles of the activated olefin, are mixed together for a sufficient of time at a temperature described above.

The progression of the reaction can be typically monitored by ESI-MS and/or NMR spectroscopy for consumption of the monomer. The reaction products can be purified or separated by HPLC or other methods known by one skilled in the art. For reactions that proceeded to completion, the formed product was separated by removal of solvent or by precipitation in a non-polar solvent that was the opposite of the reaction media. For the reactions in water, the formed product was precipitated from the aqueous reaction mixture. Higher pressure can speed-up the reaction. Typically, if the reaction is carried out at a room temperature, the reaction can have a product yield of more than 98% in 16 hours.

Additional Corrosion Control Composition Agent in a Corrosion Control Composition In addition to one or more di-cationic di-anionic compounds derived from primary amines as described herein, a corrosion control composition in the present disclosure comprises one or more additional corrosion control composition agents.

The additional corrosion control composition agent in the disclosed corrosion control compositions can include, but is not limited to, a carrier, acid, dispersant, biocide, additional corrosion inhibitor, fouling control agent, antioxidant, polymer degradation prevention agent, permeability modifier, foaming agent, antifoaming agent, fracturing proppant, scavenger for $H_2S$, $CO_2$, and/or $O_2$, gelling agent, lubricant, and friction reducing agent, salt, or mixture thereof.

The additional corrosion control composition agent in the disclosed corrosion control compositions can also include, but not be limited to, an organic sulfur compound, asphaltene inhibitor, paraffin inhibitor, scale inhibitor, water clarifier, emulsion breaker, reverse emulsion breaker, gas hydrate inhibitor, a pH modifier, a surfactant, or a combination thereof.

Furthermore, the additional corrosion control composition agent can be a sequestrant, solubilizer, lubricant, buffer, cleaning agent, rinse aid, preservative, binder, thickener or other viscosity modifier, processing aid, carrier, water-conditioning agent, or foam generator, threshold agent or system, aesthetic enhancing agent (e.g., dye, odorant, perfume), or other additive suitable for formulation with a reverse emulsion breaker, or mixtures thereof.

The additional corrosion control composition agent in a corrosion control composition disclosed herein will vary according to the specific corrosion control composition being manufactured and its intend use as one skilled in the art will appreciate.

Alternatively, the corrosion control composition does not contain or is free of one or more of the additional corrosion control composition agents.

When one or more additional corrosion control composition agents are used in the corrosion control compositions disclosed herein, they can be formulated together with the di-cationic or di-anionic compounds as described here in the same corrosion control compositions. Alternatively, some or all the additional corrosion control composition agents can be formulated into one or more different formulations and be supplied to the water systems or surfaces. In other words, the additional corrosion control composition agents can be provided into a water system or onto a surface independently, simultaneously, or sequentially.

Biocide and Carrier

In some embodiments, the corrosion control compositions disclosed herein further include a biocide, in addition to the di-cationic or di-anionic compounds. In some other embodiments, the disclosed corrosion control compositions herein further include a carrier. In some other embodiments, the disclosed corrosion control compositions herein further include a biocide and carrier. In some embodiments, the disclosed methods or corrosion control compositions herein may consist of one or more di-cationic or di-anionic compounds disclosed herein and carrier. In some embodiments, the corrosion control compositions disclosed herein consist of one or more di-cationic or di-anionic compounds disclosed herein, a carrier, and a biocide.

Biocides suitable for use may be oxidizing or non-oxidizing biocides. Oxidizing biocides include, but are not limited to, bleach, chlorine, bromine, chlorine dioxide, and materials capable of releasing chlorine and bromine. Non-oxidizing biocides include, but are not limited to, glutaraldehyde, isothiazolin, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, didecyl dimethyl ammonium chloride, poly(oxyethylene(dimethyliminio)ethylene(dimethyliminio)ethylene dichloride, methylene bisthiocyanate, 2-decylthioethanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis(tributyltin)oxide, 2-(tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo[2.2.1]heptane-2,3-dicarboxylic acid, 4,5-dichloro-2-n-octyl-4-isothiazoline-3-one, 5-chloro-2-methyl-4-isothiazolin-3-one and 2-methyl-4-isothiazolin-3-one.

Suitable non-oxidizing biocides also include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)).

Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, peroxycarboxylic acid, peroxycarboxylic acid composition, and peroxides.

The corrosion control composition can comprise from about 0.1 wt-% to about 10 wt-%, from about 0.5 wt-% to about 5 wt-%, or from about 0.5 wt-% to about 4 wt-% of a biocide, based on total weight of the composition. In some embodiments, the corrosion control composition is free of a biocide. In some embodiments, the corrosion control composition is free of an oxidizing biocide. In some other embodiments, the corrosion control composition is free of a non-oxidizing biocide.

A carrier in the disclosed corrosion control composition can be water, an organic solvent, or a combination of water and an organic solvent. The organic solvent can be an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

The corrosion control composition can comprise from about 1 wt-% to about 80 wt-%, from about 1 wt-% to about 70 wt-%, from about 1 wt-% to about 60 wt-%, from about 1 wt-% to about 50 wt-%, from about 1 wt-% to about 40 wt-%, from about 1 wt-% to about 30 wt-%, from about 1 wt-% to about 20 wt-%, from about 1 wt-% to about 10 wt-%, from about 5 wt-% to about 10 wt-%, from about 5 wt-% to about 20 wt-%, from about 5 wt-% to about 30 wt-%, from about 5 wt-% to about 40 wt-%, from about 5 wt-% to about 50 wt-%, from about 10 wt-% to about 20 wt-%, from about 10 wt-% to about 30 wt-%, from about 10 to about 40 wt-%, from about 10 wt-% to about 50 wt-%, about 10 wt-%, about 20 wt-%, about 30 wt-%, about 40-%, about 50 wt-%, about 60 wt-%, about 70 wt-%, about 80 wt-%, about 90 wt-%, or any value there between of the one or more carrier, based on total weight of the composition.

Acids

Generally, acids, as used in this disclosure, include both organic and inorganic acids. Organic acids include, but not limited to, hydroxyacetic (glycolic) acid, formic acid, acetic acid, propionic acid, butyric acid, valeric acid, caproic acid, gluconic acid, itaconic acid, trichloroacetic acid, urea hydrochloride, and benzoic acid. Organic acids also include dicarboxylic acids such as oxalic acid, malonic acid, succinic acid, glutaric acid, maleic acid, fumaric acid, adipic acid, and terephthalic acid. Combinations of these organic acids can also be used. Inorganic acids include, but are not limited to, mineral acids, such as phosphoric acid, sulfuric acid, sulfamic acid, methylsulfamic acid, hydrochloric acid, hydrobromic acid, hydrofluoric acid, and nitric acid. Inorganic acids can be used alone, in combination with other inorganic acid(s), or in combination with one or more organic acid. Acid generators can be used to form a suitable acid, including for example generators such as potassium fluoride, sodium fluoride, lithium fluoride, ammonium fluoride, ammonium bifluoride, sodium silicofluoride, etc.

Examples of particularly suitable acids in this the methods or compositions disclosed herein include inorganic and organic acids. Exemplary inorganic acids include phosphoric, phosphonic, sulfuric, sulfamic, methylsulfamic, hydrochloric, hydrobromic, hydrofluoric, and nitric. Exemplary organic acids include hydroxyacetic (glycolic), citric, lactic, formic, acetic, propionic, butyric, valeric, caproic, gluconic, itaconic, trichloroacetic, urea hydrochloride, and benzoic. Organic dicarboxylic acids can also be used such as oxalic, maleic, fumaric, adipic, and terephthalic acid.

Percarboxylic Acids and Peroxycarboxylic Acid Compositions

A peroxycarboxylic acid (i.e. peracid) or peroxycarboxylic acid composition can be included in the articles, products, or compositions disclosed herein. As used herein, the term "peracid" may also be referred to as a "percarboxylic acid," "peroxycarboxylic acid" or "peroxyacid." Sulfoperoxycarboxylic acids, sulfonated peracids and sulfonated peroxycarboxylic acids are also included within the terms "peroxycarboxylic acid" and "peracid" as used herein. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)$_n$, in which R can be hydrogen, alkyl, alkenyl, alkyne, acrylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acrylic," "alicyclic group," "aryl," "heteroaryl," and "heterocyclic group" are as defined herein.

A peroxycarboxylic acid composition, as used herein, refers to any composition that comprises one or more peracids, their corresponding acids, and hydrogen peroxide or or other oxidizing agents. A peroxycarboxylic acid composition can also include a stabilizer, fluorescent active tracer or compound, or other ingredients, as one skilled in the other would know.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid. Peracids such as peroxyacetic acid and peroxyoctanoic acid may also be used. Any combination of these acids may also be used.

Alkalinity Source

The disclosed corrosion control compositions or methods of using thereof may include using an effective amount of an alkalinity source. The alkalinity source in turn comprises one or more alkaline compounds.

In general, an effective amount of the alkalinity source should be considered as an amount that provides a reaction mixture having a pH of at least about 8. When the solution has a pH of between about 8 and about 10, it can be considered mildly alkaline, and when the pH is greater than about 12, the solution can be considered caustic.

The alkalinity source can include an alkali metal carbonate, an alkali metal hydroxide, alkaline metal silicate, alkaline metal metasilicate, or a mixture thereof. Suitable metal carbonates that can be used include, for example, sodium or potassium carbonate, bicarbonate, sesquicarbonate, or a mixture thereof. Suitable alkali metal hydroxides that can be used include, for example, sodium, lithium, or potassium hydroxide. Examples of useful alkaline metal silicates include sodium or potassium silicate (with $M_2O:SiO_2$ ratio of 2.4 to 5:1, M representing an alkali metal) or metasilicate. A metasilicate can be made by mixing a hydroxide and silicate. The alkalinity source may also include a metal borate such as sodium or potassium borate, and the like.

The alkalinity source may also include ethanolamines, urea sulfate, amines, amine salts, and quaternary ammonium. The simplest cationic amines, amine salts and quaternary ammonium compounds can be schematically drawn thus:

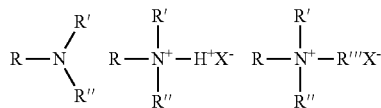

in which, R represents a long alkyl chain, R', R", and R''' may be either long alkyl chains or smaller alkyl or aryl groups or hydrogen and X represents an anion.

In some embodiments, the alkalinity source is dimethylethanolamine, methoxypropylamine, monoethanolamine, or mixture thereof.

Additional Corrosion Inhibitor

In some embodiments, the corrosion control compositions disclosed herein further include an additional corrosion inhibitor. In some other embodiments, the disclosed corrosion control compositions herein further include an additional corrosion inhibitor and carrier. In some other embodiments, the disclosed corrosion control compositions herein further include an additional corrosion inhibitor, biocide, and carrier. In some embodiments, the disclosed control compositions herein may consist of one or more di-cationic or di-anionic compounds disclosed herein, one or more additional corrosion inhibitors, and carrier. In some embodiments, the corrosion control compositions disclosed herein consist of one or more di-cationic or di-anionic compounds disclosed herein, a carrier, additional corrosion inhibitor, and biocide.

The corrosion control composition can comprise from about 0.1 wt-% to about 20 wt-%, from about 0.1 wt-% to about 10 wt-%, or from 0.1 to about 5 wt-% of the one or more additional corrosion inhibitors, based on total weight of the composition. A composition of the disclosure can comprise from 0 wt-% to 10 percent by weight of the one or more additional corrosion inhibitors, based on total weight of the composition. The composition can comprise about 1.0 wt-%, about 1.5 wt-%, about 2.0 wt-%, about 2.5 wt-%, about 3.0 wt-%, about 3.5 wt-%, about 4.0 wt-%, about 4.5 wt-%, about 5.0 wt-%, about 5.5 wt-%, about 6.0 wt-%, about 6.5 wt-%, about 7.0 wt-%, about 7.5 wt-%, about 8.0 wt-%, about 8.5 wt-%, about 9.0 wt-%, about 9.5 wt-%, about 10.0 wt-%, about 10.5 wt-%, about 11.0 wt-%, about 11.5 wt-%, about 12.0 wt-%, about 12.5 wt-%, about 13.0 wt-%, about 13.5 wt-%, about 14.0 wt-%, about 14.5 wt-%, or about 15.0 wt-% of or any value or range there between of the one or more additional corrosion inhibitors, based on total weight of the composition. A specific water system can have its own requirements for using one or more additional corrosion inhibitors, and the weight percent of one or more additional corrosion inhibitors in the composition can vary with the water system in which it is used.

Additional corrosion inhibitors for multi-metal protection are typically triazoles, such as, but not limited to, benzotriazole, halogenated triazoles, and nitro-substituted azoles.

The one or more additional corrosion inhibitors can be an imidazoline compound, a quaternary ammonium compound, a pyridinium compound, or a combination thereof.

The one or more additional corrosion inhibitors can be an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (1A) or an imidazoline derivative. Representative imidazoline derivatives include an imidazolinium compound of Formula (2A) or a bis-quaternized compound of Formula (3A).

The one or more additional corrosion inhibitors can include an imidazoline of Formula (1A):

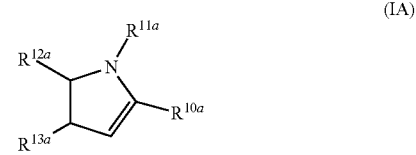

wherein $R^{10a}$ is a $C_1$-$C_{20}$ alkyl or a $C_1$-$C_{20}$ alkoxyalkyl group; $R^{11a}$ is hydrogen, $C_1$-$C_6$ alkyl, $C_1$-$C_6$ hydroxyalkyl, or $C_1$-$C_6$ arylalkyl; and $R^{12a}$ and $R^{13a}$ are independently hydrogen or a $C_1$-$C_6$ alkyl group. Preferably, the imidazoline includes an $R^{10a}$ which is the alkyl mixture typical in tall oil fatty acid (TOFA), and $R^{11a}$, $R^{12a}$ and $R^{13a}$ are each hydrogen.

The one or more additional corrosion inhibitors can be an imidazolinium compound of Formula (2A):

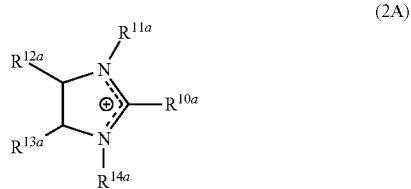

(2A)

wherein $R^{10a}$ is a $C_1$-$C_{20}$ alkyl or a $C_1$-$C_{20}$ alkoxyalkyl group; $R^{11a}$ and $R^{14a}$ are independently hydrogen, $C_1$-$C_6$ alkyl, $C_1$-$C_6$ hydroxyalkyl, or $C_1$-$C_6$ arylalkyl; $R^{12a}$ and $R^{13a}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The one or more additional corrosion inhibitors can be a bis-quaternized compound having the formula (3A):

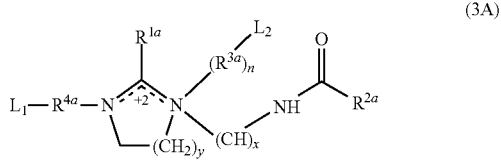

(3A)

wherein $R^{1a}$ and $R^{2a}$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof; $R^{3a}$ and $R^{4a}$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof; $L_1$ and $L_2$ are each independently absent, H, —COOH, —SO$_3$H, —PO$_3$H, —COOR$^{5a}$, —CONH$_2$, —CONHR$^{5a}$, or —CON(R$^{5a}$)$_2$; R$^{5a}$ is each independently a branched or unbranched alkyl, aryl, alkylaryl, alkylheteroaryl, cycloalkyl, or heteroaryl group having from 1 to about 10 carbon atoms; n is 0 or 1, and when n is 0, $L_2$ is absent or H; x is from 1 to about 10; and y is from 1 to about 5. Preferably, $R^{1a}$ and $R^{2a}$ are each independently $C_6$-$C_{22}$ alkyl, $C_5$-$C_{20}$ alkyl, $C_{12}$-$C_{18}$ alkyl, $C_{16}$-$C_{18}$ alkyl, or a combination thereof; $R^{3a}$ and $R^{4a}$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1; $R^3$ and $R^4$ are —C$_2$H$_2$—; $L_1$ is —COOH, —SO$_3$H, or —PO$_3$H; and $L_2$ is absent, H, —COOH, —SO$_3$H, or —PO$_3$H. For example, $R^{1a}$ and $R^{2a}$ can be derived from a mixture of tall oil fatty acids and are predominantly a mixture of $C_{17}H_{33}$ and $C_{17}H_{31}$ or can be $C_{16}$-$C_{18}$ alkyl; $R^{3a}$ and $R^{4a}$ can be $C_2$-$C_3$ alkylene such as —C$_2$H$_2$—; n is 1 and $L_2$ is —COOH or n is 0 and $L_2$ is absent or H; x is 2; y is 1; $R^{3a}$ and $R^{4a}$ are —C$_2$H$_2$—; and $L_1$ is —COOH.

It should be appreciated that the number of carbon atoms specified for each group of formula (3A) refers to the main chain of carbon atoms and does not include carbon atoms that may be contributed by substituents.

The one or more additional corrosion inhibitors can be a bis-quaternized imidazoline compound having the formula (3A) wherein $R^{1a}$ and $R^{2a}$ are each independently $C_6$-$C_{22}$ alkyl, $C_8$-$C_{20}$ alkyl, $C_{12}$-$C_{18}$ alkyl, or $C_{16}$-$C_{18}$ alkyl or a combination thereof; $R^{4a}$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —SO$_3$H, or —PO$_3$H; and $L_2$ is absent or H. Preferably, a bis-quaternized compound has the formula (3A) wherein $R^{1a}$ and $R^{2a}$ are each independently $C_{16}$-$C_{18}$ alkyl; $R^{4a}$ is —C$_2$H$_2$—; x is 2; y is 1; n is 0; $L_1$ is —COOH, —SO$_3$H, or —PO$_3$H and $L_2$ is absent or H.

The one or more additional corrosion inhibitors can be a quaternary ammonium compound of Formula (4A):

(4A)

wherein $R^{1a}$, $R^{2a}$, and $R^{3a}$ are independently $C_1$ to $C_{20}$ alkyl, $R^{4a}$ is methyl or benzyl, and $X^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula [N$^+$R$^{5a}$R$^{6a}$R$^{7a}$R$^{8a}$][X$^-$] wherein $R^{5a}$, $R^{6a}$, $R^{7a}$, and $R^{8a}$ contain one to 18 carbon atoms, and X is Cl, Br or I. For the quaternary salts, $R^{5a}$, $R^{6a}$, $R^{7a}$, and $R^{8a}$ can each be independently alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula [N$^+$R$^{5a}$R$^{6a}$R$^{7a}$R$^{8a}$][X$^-$] wherein $R^{5a}$, $R^{6a}$, $R^{7a}$, and $R^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The one or more additional corrosion inhibitors can be a pyridinium salt such as those represented by Formula (5A):

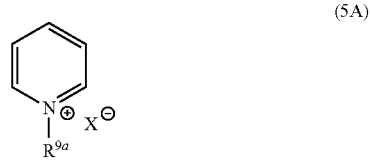

(5A)

wherein $R^{9a}$ is an alkyl group, an aryl group, or an arylalkyl group, wherein said alkyl groups have from 1 to about 18 carbon atoms and $X^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The one or more additional corrosion inhibitors can be a phosphate ester, monomeric or oligomeric fatty acid, alkoxylated amine, or mixture thereof.

The one or more additional corrosion inhibitors can be a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a broader distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The one or more additional corrosion inhibitors can be a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The one or more additional corrosion inhibitors can be an alkoxylated amine. The alkoxylated amine can be an ethoxylated alkyl amine. The alkoxylated amine can be ethoxylated tallow amine.

In some embodiments, the additional corrosion inhibitor in the corrosion control composition is tall oil diethylenetriamine imidazoline, 1-(2-hydroxyethyl)-2-coconut oil-2-imidazoline, 1-benzyl-1-(2-hydroxyethyl)-2-coconut oil-2-imidazolinium chloride, benzyl-dimethyl-dodecyl-ammonium chloride, N-coco alkyl 1,3, propylenediamine acetate, morpholine, morpholine derivative, didecyl-dimethyl-ammonium chloride, 1-benzyl-1-(2-hydroxyethyl)-2-tall oil-2-imidazolinium chloride, and N-benzyl-alkylpyridinium chloride. tall oil fatty acid, trimeric C18 unsaturated fatty acid, dimeric C18 unsaturated fatty acid, alkylpyridine, N-benzyl-alkylpyridinium chloride, quinoline, quinoline quaternary compound with benzyl chloride, or mixture thereof.

Dispersant

In some embodiments, the corrosion control compositions disclosed herein can further comprise a dispersant. A dispersant keeps particulate matter present in the water of a water system dispersed, so that it does not agglomerate. The composition can comprise from about 0.1 to 10 wt-%, from about 0.5 to 5 wt-%, or from about 0.5 to 4 wt-% of a dispersant, based on total weight of the composition.

A dispersant may be an acrylic acid polymer, maleic acid polymer, copolymer of acrylic acid with sulfonated monomers, alkyl esters thereof, or combination thereof. These polymers may include terpolymers of acrylic acid, acrylamide and sulfonated monomers. These polymers may also include quad-polymers consisting of acrylic acid and three other monomers.

Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

In some embodiments, the dispersant in the corrosion control compositions disclosed herein is a reaction product of tall oil fatty acids with diethylenetriamine and acrylic acid (1:1:1), reaction product of fatty acids or tall-oil with triethylenetetramine or tetraethylenepentamine, reaction product of diethylenetriamine and napthenic acid.

The corrosion control composition can further comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. Such compounds are used as synergists in the composition.

In some embodiments, the organic sulfur compound in the corrosion control composition is 2 Mercaptoethanol, sodium thiosulfate, thioglycolic acid, or a mixture thereof.

The organic sulfur compound can constitute from about 0.5 wt-% to about 15 wt-% of the composition, based on total weight of the composition, preferably from about 1 wt-% to about 10 wt-% and more preferably from about 1 wt-% to about 5 wt-%. The organic sulfur compound can constitute about 1 wt-%, about 2 wt-%, about 3 wt-%, about 4 wt-%, about 5 wt-%, about 6 wt-%, about 7 wt-%, about 8 wt-%, about 9 wt-%, about 10 wt-%, about 11 wt-%, about 12 wt-%, about 13 wt-%, about 14 wt-%, or about 15 wt-% of the composition.

The corrosion control composition can further comprise a de-emulsifier. Preferably, the demulsifier comprises an oxyalkylate polymer, such as a polyalkylene glycol. The de-emulsifier can constitute from about 0.1 wt-% to about 10 wt-%, from about 0.5 wt-% to about 5 wt. %, or from about 0.5 wt-% to about 4 wt-% of the composition, based on total weight of the composition. The de-emulsifier can constitute about 0.5 wt-%, about 1 wt-%, about 1.5 wt-%, about 2 wt-%, about 2.5 wt-%, about 3 wt-%, about 3.5 wt-%, about 4 wt-%, about 4.5 wt-%, or about 5 wt-% of the composition.

The corrosion control composition can further comprise an asphaltene inhibitor. The composition can comprise from about 0.1 wt-% to about 10 wt-%, from about 0.1 wt-% to about 5 wt-%, or from about 0.5 wt-% to about 4 wt-% of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The corrosion control composition can further comprise a paraffin inhibitor. The composition can comprise from about 0.1 wt-% to about 10 wt-%, from about 0.1 wt-% to about 5 wt-%, or from about 0.5 wt-% to about 4 wt-% of a paraffin inhibitor, based on total weight of the composition. Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The corrosion control composition can further comprise a scale inhibitor. The composition can comprise from about 0.1 wt-% to about 20 wt-%, from about 0.5 wt-% to about 10 wt-%, or from about 1 wt-% to about 10 wt-% of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), mono-, bis- and oligomeric phosphinosuccinic acid (PSO) derivatives, polycarboxylic acid, hydrophobically modified polycarboxylic acid, and salts of a polymaleic acid/acrylic acid/acrylamidomethyl propane sulfonate terpolymer (PMA/AA/AMPS).

The corrosion control composition can further comprise an emulsifier. The composition can comprise from about 0.1 wt-% to about 10 wt-%, from about 0.5 wt-% to about 5 wt-%, or from about 0.5 wt-% to about 4 wt-% of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

The corrosion control composition can further comprise a water clarifier. The composition can comprise from about 0.1 wt-% to about 10 wt-%, from about 0.5 wt-% to about 5 wt-%, or from about 0.5 wt-% to about 4 wt-% of a water clarifier, based on total weight of the composition. Suitable water clarifiers include, but are not limited to, inorganic metal salts such as alum, aluminum chloride, and aluminum chlorohydrate, or organic polymers such as acrylic acid-based polymers, acrylamide-based polymers, polymerized amines, alkanolamines, thiocarbamates, and cationic polymers such as diallyldimethylammonium chloride (DADMAC).

The corrosion control composition can further comprise an emulsion breaker. The composition can comprise from about 0.1 wt-% to about 10 wt-%, from about 0.5 wt-% to about 5 wt-%, or from about 0.5 wt-% to about 4 wt-% of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, and resins, such as phenolic and epoxide resins.

The corrosion control composition can further comprise a hydrogen sulfide scavenger. The composition can comprise from about 1 wt-% to about 50 wt-%, from about 1 wt-% to about 40 wt-%, from about 1 wt-% to about 30 wt-%, from about 0.1 wt-% to about 10 wt-%, from about 0.5 wt-% to about 5 wt-%, or from about 0.5 wt-% to about 4 wt-% of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The corrosion control composition can further comprise a gas hydrate inhibitor. The composition can comprise from about 0.1 wt-% to about 25 wt-%, from about 0.5 wt-% to about 20 wt-%, from about 1 wt-% to about 10 wt-%, from about 0.1 wt-% to about 10 wt-%, from about 0.5 wt-% to about 5 wt-%, or from about 0.5 wt-% to about 4 wt-% of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The corrosion control composition can further comprise a kinetic hydrate inhibitor. The composition can comprise from about 0.1 wt-% to about 25 wt-%, from about 0.5 wt-% to about 20 wt-%, from about 1 wt-% to about 10 wt-%, from about 0.1 wt-% to about 10 wt-%, from about 0.5 wt-% to about 5 wt-%, or from about 0.5 wt-% to about 4 wt-% of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines, hydrocarbon based dispersants (such as lignosulfonates, iminodisuccinates, polyaspartates), amino acids, and proteins.

The corrosion control composition can further comprise a pH modifier. The composition can comprise from about 0.1 wt-% to about 20 wt-%, from about 0.5 wt-% to about 10 wt-%, or from about 0.5 wt-% to about 5 wt-% of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The corrosion control composition can further comprise a surfactant. The composition can comprise from about 0.1 wt-% to about 10 wt-%, from about 0.5 wt-% to about 5 wt-%, or from about 0.5 wt-% to about 4 wt-% of a surfactant, based on total weight of the composition. A suitable surfactant can be a nonionic, semi-nonionic, cationic, anionic, amphoteric, zwitterionic, Gemini, di-cationic, di-anionic surfactant, or mixtures thereof. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, block copolymers of ethylene and propylene, propylene and butylene oxides, alkyl dimethyl amine oxides, alkyl-bis(2-hydroxyethyl) amine oxides, alkyl amidopropyl dimethyl amine oxides, alkylamidopropyl-bis (2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

In some embodiments, the surfactant is phosphate esters of ethoxylated C10-C16 alcohols, ethoxylated C11-C14 iso or C13 rich phosphates, ethoxylated nonylphenol, ethoxylated branched nonylphenol, or mixture thereof.

The corrosion control composition can further comprise other additional corrosion control composition agents that provide a functional and/or beneficial property. For example, additional corrosion control composition agent can be a sequestrant, solubilizer, lubricant, buffer, cleaning agent, rinse aid, preservative, binder, thickener or other viscosity modifier, processing aid, water-conditioning agent, foam inhibitor or foam generator, threshold agent or system, aesthetic enhancing agent (e.g., dye, odorant, perfume), or other agentd suitable for formulation with the corrosion inhibitor composition, and mixtures thereof. Additional agents vary according to the specific corrosion control composition being manufactured and its intend use as one skilled in the art will appreciate.

Alternatively, the corrosion control composition does not contain or is free of any of the additional corrosion control composition agents.

Additionally, the corrosion control composition can be formulated into exemplary compositions comprising the following components as shown in Table 1. These formulations include the ranges of the components listed and can optionally include additional corrosion control composition agents. The values in the Table 1 below are weight percentages.

TABLE 1

Exemplary Corrosion Control Compositions

| Component | 1 | 2 | 3 | 4 | 5 | 6 | 7 | 8 | 9 | 10 | 11 | 12 |
|---|---|---|---|---|---|---|---|---|---|---|---|---|
| Di-cationic or di-anionic compounds | 0.1-20 | 0.1-20 | 0.1-20 | 0.1-20 | 0.1-20 | 0.1-20 | 10-20 | 10-20 | 10-20 | 10-20 | 10-20 | 0.1-20 |
| Carrier | 5-40 | — | 5-50 | — | 5-50 | 5-50 | 5-40 | — | 5-50 | — | — | 10-20 |
| additional corrosion inhibitor | 0.1-20 | 0.1-20 | — | — | — | — | 0.1-20 | 0.1-20 | — | — | — | 0.1-20 |
| Organic sulfur compound | 0.1-5 | 0.1-5 | 0.1-5 | 0.1-5 | — | — | 0.1-5 | 0.1-5 | 0.1-5 | — | — | 0.1-5 |
| Scale inhibitor | 1-10 | 1-10 | 1-10 | 1-10 | 1-10 | — | 1-10 | 1-10 | 1-10 | 1-10 | — | 1-10 |
| surfactant | — | — | — | — | — | — | — | — | — | — | — | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | — |
| Water | 0.00 | 0-40 | 0-10 | 0-60 | 0-15 | 0-25 | 0.00 | 0-40 | 0-10 | 0-65 | 0-75 | — |

| Component | 13 | 14 | 15 | 16 | 17 | 18 | 19 | 20 | 21 | 22 | 23 | 24 |
|---|---|---|---|---|---|---|---|---|---|---|---|---|
| Di-cationic or di-anionic compounds | 0.1-20 | 0.1-20 | 0.1-20 | 0.1-20 | 0.1-20 | 0.1-20 | 10-20 | 10-20 | 10-20 | 10-20 | 10-20 | 10-20 |
| carrier | — | 10-20 | — | 10-35 | 10-35 | — | 10-15 | — | — | 10-35 | 10-35 | — |
| Additional corrosion inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Organic sulfur compound | 0.1-5 | — | — | — | — | — | 0.1-5 | — | — | — | — | — |
| Scale inhibitor | 1-10 | 1-10 | — | — | 1-10 | — | 1-10 | 1-10 | — | — | — | 1-10 |
| surfactant | 0.1-25 | 0.1-25 | 0.1-25 | — | — | — | 0.1-25 | 0.1-25 | 0.1-25 | — | 0.1-25 | — |
| Biocide | — | — | — | — | — | 0.5-5 | 0.5-5 | 0.5-5 | 0.5-5 | 0.5-5 | — | — |
| Water | 0-20 | 0-5 | 0-35 | 0-25 | 0-15 | 0-55 | 0.00 | 0-20 | 0-30 | 0-20 | 0.00 | 0-50 |

Water System

The corrosion control composition or its use solution is applied to a water system to prevent corrosion on surfaces in the water system or onto surfaces within the water system.

In some embodiments, the water system in the disclosed methods herein is an industrial water system. In other embodiments, the water system can be, but is not limited to, a cooling water system, including an open recirculating system, closed and once-through cooling water system, boilers and boiler water system, petroleum well system, downhole formation, geothermal well, and other water system in oil and gas field applications, a mineral washing system, flotation and benefaction system, paper mill digester, washer, bleach plant, stock chest, white water system, paper machine surface, black liquor evaporator in the pulp industry, gas scrubber and air washer, continuous casting processes in the metallurgical industry, air conditioning and refrigeration system, industrial and petroleum process water, indirect contact cooling and heating water, water reclamation system, water purification system, membrane filtration water system, food processing stream (meat, vegetable, sugar beets, sugar cane, grain, poultry, fruit and soybean), waste treatment system, clarifier, liquid-solid application, municipal sewage treatment, municipal water system, potable water system, aquifer, water tank, sprinkler system, or water heater.

The water system can be those used in oil and gas operations. The water system can comprise water, oil, and solid. In some embodiments, the water system comprises mostly oil or hydrocarbons. For example, the water systems include oil or gasoline in tanks or pipelines. In some embodiments, the water system is one used in oil and gas operations.

In some embodiments, the water system is a cooling water system, including open recirculating, closed and once-through cooling water system, paper machine surface, food processing stream, waste treatment system, or potable water system.

Use of the Methods or Compositions Disclosed

In some embodiments, for the methods disclosed herein, providing a corrosion control composition into a water system means that the corrosion control composition, one or more di-cationic or di-anionic compounds, or a use solution thereof is added into a fluid comprising water or onto a surface of a water system. In other embodiments, providing a corrosion control composition into a water system means adding the corrosion control composition or the di-cationic or di-anionic compounds onto the surface or into the water of the water system. In some other embodiments, providing a corrosion control composition into a water system means adding the corrosion control composition, di-cationic or di-anionic compounds, or use solution thereof to a fluid or gas that in turn contacts the surfaces of the water system. The corrosion control composition, di-cationic or di-anionic compounds, or use solution thereof may be added continuously, or intermittently when more compounds or compositions may be needed.

A use solution of a corrosion control composition or of one or more di-cationic or di-anionic compounds as used herein refers to a diluted solution for the composition or compounds by a diluent. A diluent as used herein refers to water, the water of a water system, or one of the carriers or solvents defined herein. The corrosion control composition or the compounds can be diluted by a factor of 0.5, 1, 2, 3, 4, 5, 6, 7, 8, 9, 10, 11-1,000,000, or any value there between to generate a use solution and then provide the use solution to a water system or onto a surface. In this disclosure, when a composition or di-cationic or di-anionic compounds are applied, either the composition/compounds or use solution thereof is applied.

In some embodiments, the corrosion control composition or the di-cationic or di-anionic compounds disclosed herein may be added to the water of the water system, so the concentration of the composition or compounds in the treated water system is in an concentration of from about 1 ppm to about 1000 ppm. In other embodiments, the amount of the corrosion control composition or the di-cationic or di-anionic compounds in the water of the water system may range from about 5 ppm to about 100 ppm, about 5 ppm to about 50 ppm, about 5 ppm to about 40 ppm, about 5 ppm to about 30 ppm, about 10 ppm to about 60 ppm, about 10 ppm to about 50 ppm, about 10 ppm to about 40 ppm, about 10 ppm to about 30 ppm, about 20 ppm to about 60 ppm, about 20 ppm to about 50 ppm, about 20 ppm to about 40 ppm, or about 20 ppm to about 30 ppm. In some embodiments, the corrosion control composition or the di-cationic or di-anionic compounds may be added to the water to an amount ranging from about 100 ppm to about 1000 ppm, about 125 ppm to about 1000 ppm, about 250 ppm to about 1000 ppm, or about 500 ppm to about 1000 ppm.

The corrosion control composition or the di-cationic or di-anionic compounds can be used for corrosion control in oil and gas applications such as by treating a gas or liquid stream with an effective amount of the compound or composition as described herein. The compounds and compositions can be used in any industry where it is desirable to prevent corrosion at a surface.

The corrosion control composition or the di-cationic or di-anionic compounds can be used in a condensate/oil systems/gas system, or any combination thereof. For example, the corrosion control composition or the di-cationic or di-anionic compounds can be used in corrosion control on heat exchanger surfaces. The corrosion control composition or the di-cationic or di-anionic compounds can be applied to a gas or liquid produced, or used in the production, transportation, storage, and/or separation of crude oil or natural gas. The corrosion control composition or the di-cationic or di-anionic compounds can be applied to a gas stream used or produced in a coal-fired process, such as a coal-fired power plant.

The corrosion control composition or the di-cationic or di-anionic compounds can be applied to a gas or liquid produced or used in a waste-water process, a farm, a slaughter house, a land-fill, a municipality waste-water plant, a coking coal process, or a biofuel process.

A fluid to which the corrosion control composition or the di-cationic or di-anionic compounds can be introduced can be an aqueous medium. The aqueous medium can comprise water, gas, and optionally liquid hydrocarbon.

A fluid to which the corrosion control composition or the di-cationic or di-anionic compounds can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. The fluid or gas can be a refined hydrocarbon product.

A fluid or gas treated with the corrosion control composition or the di-cationic or di-anionic compounds can be at any selected temperature, such as ambient temperature or an elevated temperature. The fluid (e.g., liquid hydrocarbon) or gas can be at a temperature of from about 40° C. to about 250° C. The fluid or gas can be at a temperature of from about −50° C. to about 300° C., from about 0° C. to about 200° C., from about 10° C. to about 100° C., or from about 20° C. to about 90° C. The fluid or gas can be at a temperature of about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. The fluid or gas can be at a temperature of about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or about 100° C.

The corrosion control composition or the di-cationic or di-anionic compounds can be added to a fluid (or water system) at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The fluid or gas of a water system or the water of a water system, in which the corrosion control composition or the di-cationic or di-anionic compounds are introduced, can be contained in and/or exposed to many types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vespels, or processing units.

The corrosion control composition or the di-cationic or di-anionic compounds can be introduced into a fluid or gas of the water system by any appropriate method for ensuring dispersal through the fluid or gas. For examples, the corrosion control composition or the di-cationic or di-anionic compounds can be added to the hydrocarbon fluid before the hydrocarbon fluid contacts the surface.

The corrosion control composition or the di-cationic or di-anionic compounds can be added at a point in a flow line upstream from the point at which corrosion control is desired. The corrosion control composition or the di-cationic or di-anionic compounds can be injected using mechanical equipment such as chemical injection pumps, piping tees, injection fittings, atomizers, quills, and the like.

The corrosion control composition or the di-cationic or di-anionic compounds can be pumped into an oil and/or gas pipeline using an umbilical line. A capillary injection system can be used to deliver the corrosion control composition or the di-cationic or di-anionic compounds to a selected fluid.

A fluid to which the corrosion control composition or the di-cationic or di-anionic compounds can be introduced can be an aqueous medium. The aqueous medium can comprise water, gas, and optionally liquid hydrocarbon. A fluid to which the corrosion control composition or the di-cationic or di-anionic compounds can be introduced can be a liquid hydrocarbon.

The corrosion control composition or the di-cationic or di-anionic compounds can be introduced into a liquid and a mixture of several liquids, a liquid and gas, liquid, solid, and gas. The corrosion control composition or the di-cationic or di-anionic compounds can be injected into a gas stream as an aqueous or non-aqueous solution, mixture, or slurry.

The fluid or gas can be passed through an absorption tower comprising the corrosion control composition or the di-cationic or di-anionic compounds.

The corrosion control composition or the di-cationic or di-anionic compounds can be applied to a fluid or gas to provide any selected concentration. In practice, the corrosion control composition or the di-cationic or di-anionic compounds are typically added to a flow line to provide an effective treating dose of the corrosion control composition or the di-cationic or di-anionic compounds from about 0.01 ppm to about 5,000 ppm. The corrosion control composition or the di-cationic or di-anionic compounds can be applied to a fluid or gas to provide an active concentration of about 1 parts per million (ppm) to about 1,000,000 ppm, about 1 parts per million (ppm) to about 100,000 ppm, or about 10 ppm to about 75,000 ppm. The polymer salts/compositions can be applied to a fluid to provide an actives concentration of about 100 ppm to about 10,000 ppm, about 200 ppm to about 8,000 ppm, or about 500 ppm to about 6,000 ppm. The actives concentration means the concentration of corrosion control composition or the di-cationic or di-anionic compounds.

The corrosion control composition or the di-cationic or di-anionic compounds can be applied to a fluid or gas to provide an active concentration of about 0.1 ppm, about 0.5 ppm, about 1 ppm, about 2 ppm, about 5 ppm, about 10 ppm, about 20 ppm, about 100 ppm, about 200 ppm, about 500 ppm, or about 1,000 ppm in the treated fluid or gas, e.g., the treated water system. The corrosion control composition or the di-cationic or di-anionic compounds can be applied to a fluid or gas or water system to provide an actives concentration of about 0.125 ppm, about 0.25 ppm, about 0.625 ppm, about 1 ppm, about 1.25 ppm, about 2.5 ppm, about 5 ppm, about 10 ppm, or about 20 ppm in the treated fluid, gas, or water system. Each water system can have its own dose level requirements, and the effective dose level of the corrosion control composition or the di-cationic or di-anionic compounds to sufficiently reduce the rate of microbial or biofilm growth can vary with the water system in which it is used.

The corrosion control composition or the di-cationic or di-anionic compounds can be applied continuously, in batch, or a combination thereof. The corrosion control composition or the di-cationic or di-anionic compounds dosing can be continuous. The corrosion control composition or the di-cationic or di-anionic compounds dosing can be intermittent (e.g., batch treatment) or can be continuous/maintained and/or intermittent.

Dosage rates for continuous treatments typically range from about 10 ppm to about 500 ppm, or about 10 ppm to about 200 ppm. Dosage rates for batch treatments typically range from about 10 ppm to about 400,000 ppm, or about 10 ppm to about 20,000 ppm. The corrosion control composition or the di-cationic or di-anionic compounds can be applied as a pill to a pipeline, providing a high dose (e.g., 20,000 ppm) of the composition.

The flow rate of a flow line in which the corrosion control composition or the di-cationic or di-anionic compounds is used can be between about 0.1 feet per second and about 1,000 feet per second, or between about 0.1 feet per second and about 50 feet per second. The corrosion control composition or the di-cationic or di-anionic compounds can also be formulated with water to facilitate addition to the flow line.

A surface of a water system can be any surface that can make contact to the water or vapor of the water of the water system in any way. The surface can be a part of a wellbore or equipment used in the production, transportation, storage, and/or separation of a fluid such as crude oil or natural gas.

More specifically, the surface can be a part of equipment used a coal-fired process, a waste-water process, a farm, a slaughter house, a land-fill, a municipality waste-water plant, a coking coal process, or a biofuel process. Preferably, the surface can be a part of equipment used in the production of crude oil or natural gas.

The equipment can comprise a pipeline, a storage vessel, downhole injection tubing, a flow line, or an injection line.

The corrosion control composition or the di-cationic or di-anionic compounds are useful for prevention corrosion of containers, processing facilities, or equipment in the food service or food processing industries. The corrosion control composition or the di-cationic or di-anionic compounds have particular value for use on food packaging materials and equipment, and especially for cold or hot aseptic packaging. Examples of process facilities in which the corrosion control composition or the di-cationic or di-anionic compounds can be employed include a milk line dairy, a continuous brewing system, food processing lines such as pumpable food systems and beverage lines, ware wash machines, low temperature ware wash machines, dishware, bottle washers, bottle chillers, warmers, third sink washers, processing equipment such as tanks, vats, lines, pumps and hoses (e.g., dairy processing equipment for processing milk, cheese, ice cream and other dairy products), and transportation vehicles. The corrosion control composition or the di-cationic or di-anionic compounds can be used to inhibit corrosion in tanks, lines, pumps, and other equipment used for the manufacture and storage of soft drink materials, and also used in the bottling or containers for the beverages.

The corrosion control composition or the di-cationic or di-anionic compounds can also be used on or in other industrial equipment and in other industrial process streams such as heaters, cooling towers, boilers, retort waters, rinse waters, aseptic packaging wash waters, and the like. The corrosion control composition or the di-cationic or di-anionic compounds can be used to treat surfaces in recreational waters such as in pools, spas, recreational flumes and water slides, fountains, and the like.

The corrosion control composition or the di-cationic or di-anionic compounds can be used to treat metal surfaces contacted with cleaners in surfaces found in janitorial and/or housekeeping applications, food processing equipment and/or plant applications, and in laundry applications. For example, washers, such as tunnel washers for washing textiles, can be treated according to methods disclosed herein.

The corrosion control composition or the di-cationic or di-anionic compounds can be used or applied in combination with low temperature dish and/or warewash sanitizing final rinse, toilet bowl cleaners, and laundry bleaches. The corrosion control composition or the di-cationic or di-anionic compounds can be used to treat metal surfaces, such as ware, cleaned and/or sanitized with corrosive sources.

The corrosion control composition or the di-cationic or di-anionic compounds can be dispensed in any suitable method generally known by one skilled in the art. For example, a spray-type dispenser can be used. A spray-type dispenser functions by impinging a water spray upon an exposed surface of a composition to dissolve a portion of the composition, and then immediately directing the concentrate solution including the composition out of the dispenser to a storage reservoir or directly to a point of use.

The corrosion control composition or the di-cationic or di-anionic compounds can be dispensed by immersing either intermittently or continuously in the water, fluid, or gas of the water system. The corrosion control composition or the di-cationic or di-anionic compounds can then dissolve, for example, at a controlled or predetermined rate. The rate can be effective to maintain a concentration of the dissolved compounds or compositions that are effective for use according to the methods disclosed herein.

The corrosion control composition disclosed herein can comprise from about 10 wt-% to about 90 wt-% of the carrier, biocide, additional corrosion inhibitor, additional corrosion control composition agent, or a combination thereof and from about 10 wt-% to about 90 wt-% of one or more di-cationic or di-anionic compounds, from about 20 wt-% to about 80 wt-% of the carrier, biocide, additional corrosion inhibitor, additional corrosion control composition agent, or a combination thereof and from about 20 wt-% to about 80 wt-% of one or more di-cationic or di-anionic compounds; from about 30 wt-% to about 70 wt-% of the carrier, biocide, additional corrosion inhibitor, additional corrosion control composition agent, or a combination thereof and from about 30 wt-% to about 70 wt-% of the one or more di-cationic or di-anionic compounds, or from about 40 wt-% to about 60 wt-% of the carrier, biocide, additional corrosion inhibitor, additional corrosion control composition agent, or a combination thereof and from about 40 to about 60 wt. % of the one or more di-cationic or di-anionic compounds.

In one aspect, disclosed herein is a corrosion control composition, the composition comprises one or more compounds according to one of Formula I, Formula II, Formula III and one or more additional corrosion control composition agents,

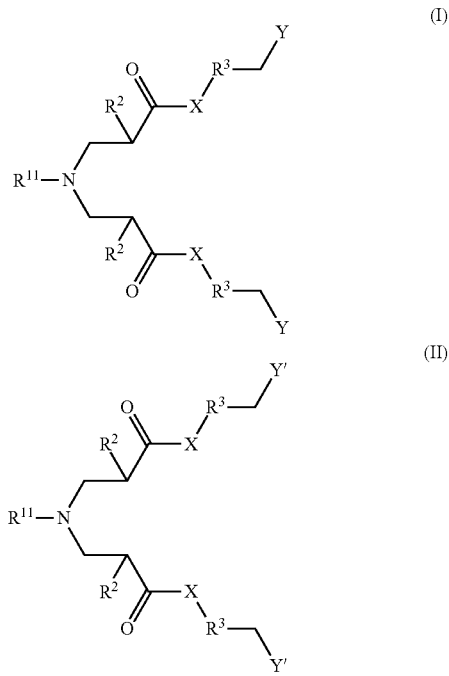

-continued

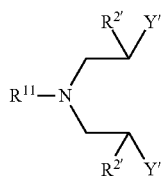

(III)

wherein X is NH or O; $R^{11}$ is $R^1$ or $R^1$—Z—$(CH_2)_m$—; $R^1$ is an unsubstituted or substituted, linear or branched $C_1$-$C_{30}$ alkyl, cyclic alkyl, alkenyl, or alkynyl group; Z is NH or O; $R^2$ is H, $CH_3$, or an unsubstituted, linear or branched $C_2$-$C_{10}$ alkyl, alkenyl, or alkynyl group; m is an integer of 1 to 4; $R^3$ is absent or an unsubstituted, linear $C_1$-$C_{30}$ alkylene group; Y is —N $R^4R^5R^{6(+)}$; Y' is —COOH, —$SO_3H$, —$PO_3H$, —$OSO_3H$, —$OPO_3H$, or a salt thereof; $R^{2'}$ is H, $CH_3$, or an unsubstituted or substituted, linear or branched $C_1$-$C_{10}$ alkyl, alkenyl, alkynyl group, —COOH, —$CH_2COOH$, Y', or —$(CH_2)_m$—Y'; and $R^4$, $R^5$, and $R^6$ are independently a $C_1$-$C_{10}$ alkyl group, and wherein the corrosion control composition mitigates corrosion on the surface in the water system.

In another aspect, disclosed herein is a method for inhibiting corrosion at a surface in a water system, the method comprises providing a corrosion control composition or a use solution of the corrosion control composition into a water system to generate a treated water system or onto a surface of the water system, wherein the corrosion control composition comprises one or more compounds according to one of Formula I, Formula II, Formula III and one or more additional corrosion control composition agents,

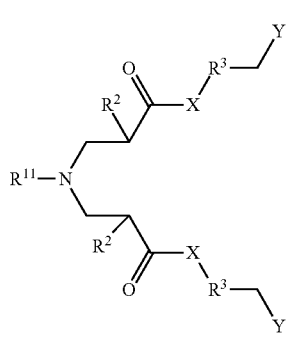

(I)

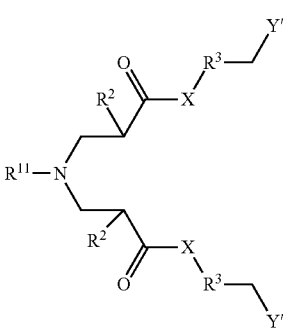

(II)

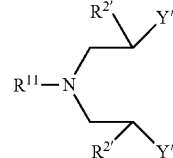

(III)

wherein X is NH or O; $R^{11}$ is $R^1$ or $R^1$—Z—$(CH_2)_m$—; $R^1$ is an unsubstituted or substituted, linear or branched $C_5$-$C_{30}$ alkyl, cyclic alkyl, alkenyl, or alkynyl group; Z is NH or O; $R^2$ is H, $CH_3$, or an unsubstituted, linear or branched $C_2$-$C_{10}$ alkyl, alkenyl, or alkynyl group; m is an integer of 1 to 4; $R^3$ is absent or an unsubstituted, linear $C_1$-$C_{30}$ alkylene group; Y is —$NR_4R_5R_6^{(+)}$; Y' is —COOH, —$SO_3H$, —$PO_3H$, —$OSO_3H$, —$OPO_3H$, or a salt thereof; $R^{2'}$ is H, $CH_3$, or an unsubstituted or substituted, linear or branched $C_1$-$C_{10}$ alkyl, alkenyl, alkynyl group, —COOH, —$CH_2COOH$, Y', or —$(CH_2)_m$—Y'; and $R^4$, $R^5$, and $R^6$ are independently a $C_1$-$C_{10}$ alkyl group, and wherein the corrosion control composition mitigates corrosion on the surface in the water system.

In some embodiments, the corrosion control composition can mitigate corrosion on a metal surface to about 280 mpy, about 265, about 250 mpy, about 225 mpy, about 200 mpy, about 175 mpy, about 150 mpy, about 175 mpy, about 100 mpy, or any value there between, when the di-cation or di-anionic compound is at about 2 ppm and corrosion rate is measured by a bubble test.

In some embodiments, the one or more compounds are one or more of Formula I. In some other embodiments, the one or more compounds are one or more of Formula II. In yet some other embodiments, the one or more compounds are one or more of Formula III. In some other embodiments, the one or more compounds are one or more of Formula II and Formula III.

In some embodiments of the disclosed compounds herein, X is NH. In some other embodiments, X is O.

In some embodiments, $R^{11}$ is $R^1$. In some other embodiments, $R^{11}$ is $R^1$—Z—$(CH_2)_m$—. In some embodiments, $R^{11}$ is $R^1$—Z—$(CH_2)_m$—, and Z is NH. In some other embodiments, $R^{11}$ is $R^1$—Z—$(CH_2)_m$—, and Z is O. In yet some other embodiments, $R^{11}$ is $R^1$—Z—$(CH_2)_m$—, Z is NH, m is 2.

In some embodiments, $R^2$ is H. In some embodiments, $R^2$ is $CH_3$. In yet some other embodiments, $R^2$ is $CH_3CH_3$, $CH_2CH_2CH_3$, or $CH(CH_3)_2$.

In some embodiments, Y is —N $R^4R^5R^{6(+)}$. In some other embodiments, Y is —N $R^4R^5R^{6(+)}$, and $R^4$, $R^5$, and $R^6$ are independently $CH_3$. In yet some other embodiments, Y is —N $R^4R^5R^{6(+)}$, and $R^4$ and $R^5$, independently $CH_3$, and $R^6$ is a $C_2$-$C_{12}$ aromatic alkyl. In some other embodiments, Y is —N $R^4R^5R^{6(+)}$, and $R^4$ and $R^5$, independently $CH_3$, and $R^6$ is —$CH_2$—$C_6H_5$.

In some embodiments, Y is —N $R^4R^5R^{6(+)}$ and the counter ion for Y any negative charged ion or species. In some other embodiments, the counter ion for Y is chloride, bromide, fluoride, iodide, acetate, aluminate, cyanate, cyanide, dihydrogen phosphate, dihydrogen phosphite, formate, carbonate, hydrogen carbonate, hydrogen oxalate, hydrogen sulfate, hydroxide, nitrate, nitrite, thiocyanate, or a combination thereof.

In some embodiments, Y is —COOH or salt thereof. In some other embodiments, Y is —$SO_3H$, —$OSO_3H$, or salt thereof. In yet some other embodiments, Y is —$PO_3H$, —OPO$_3$H, or salt thereof. In some other embodiments, Y is an acidic species or salt thereof.

In some embodiments, R$^3$ is CH$_2$. In some other embodiments, R$^3$ is CH$_2$CH$_2$. In other embodiments, R$^3$ is C(CH$_3$)$_2$. In yet some other embodiments, R$^3$ is an unsubstituted, linear, and saturated C$_2$-C$_{10}$ alkylene group. In some embodiments, R$^3$ is an unsubstituted, linear, and unsaturated C$_2$-C$_{10}$ alkylene group.

In some embodiments, R$^1$ is a linear C$_5$-C$_{30}$ alkyl, alkenyl, or alkynyl group. In some other embodiments, R$^1$ is a branched C$_5$-C$_{30}$ alkyl, alkenyl, or alkynyl group. In yet some other embodiments, R$^1$ is a linear and saturated C$_5$-C$_{30}$ alkyl group. In some other embodiments, R$^1$ is a branched and saturated C$_5$-C$_{30}$ alkyl group.

In some embodiments, R$^1$ is a linear C$_1$-C$_{30}$ alkenyl group with one or more double bonds. In some other embodiments, wherein R$^1$ is a branched C$_3$-C$_{30}$ alkenyl group with one or more double bonds.

In some embodiments, R$^1$ is a linear C$_3$-C$_{30}$ alkynyl group with one or more triple bonds. In some other embodiments, R$^1$ is a branched C$_3$-C$_{30}$ alkynyl group With one or more triple bonds.

In some embodiments, R$^{11}$ is a linear and saturated C$_1$-C$_{20}$ alkyl group. In some other embodiments, R$^{11}$ is a trans C$_3$-C$_{20}$ alkenyl group with at least one double bond. In some other embodiments, R$^{11}$ is a C$_3$-C$_{20}$ alkenyl group with at least one double bond of trans configuration. In some embodiments, R$^{11}$ is a cis C$_3$-C$_{20}$ alkenyl group with at least one double bond. In some other embodiments, R$^{11}$ is a C$_3$-C$_{20}$ alkenyl group with at least one double bond of cis configuration.

In some embodiments, R$^{11}$ is R$^1$—NH—CH$_2$CH$_2$CH$_2$ group and R$^1$ is a linear and saturated C$_6$-C$_{20}$ alkyl, a trans alkenyl, or a cis alkenyl group.

In some other embodiments, R$^2$ is H, X is NH, R$^3$ is CH$_2$CH$_2$, Y is CH$_2$—N$^+$(CH$_3$)$_3$Cl$^-$.

In some embodiments, the compound is a mixture of two or more di-cationic or anionic compounds. In some other embodiments, the compound is a single or mixture of di-cationic compounds. In some other embodiments, the compound is a single or mixture of di-anionic compounds. The two or more di-cationic or anionic compounds are different from each other by molecular or average molecular weight, structure or combination thereof.

In some embodiments, the compound is a mixture of at least two different di-cationic compounds derived from the same primary amine and activated olefin or from different primary amines and activated olefins.

In some embodiments, the compound is derived from a primary amine and (3-Acrylamidopropyl)trimethylammonium chloride (APTAC). In some other embodiments, the compound is derived from a primary amine and [3-(methacryloylamino)propyl]trimethylammonium chloride (MAPTAC).

In some embodiments, the compound is derived from a primary amine and a activated olefin. In some embodiments, the activated olefin is (3-Acrylamidopropyl)trimethylammonium chloride (APTAC), [3-(Methacryloylamino)propyl]trimethylammonium chloride (MAPTAC), 2-(acryloyloxy)-N,N,N-trimethylethanaminium chloride (DMAEA-MCQ), N,N-dimethylaminoethyl acrylate benzyl chloride quaternary salt (DMAEA-BCQ), 2-(methacryloyloxy)-N,N,N-trimethylethan-1-aminium methyl sulfate (DMAEA-MSQ), or 2-(acryloyloxy)-N,N,N-trimethylethanaminium chloride (DMAEA-MSQ).

In some other embodiments, the activated olefin is (3-Acrylamidopropyl)trimethylammonium chloride (APTAC), [3-(Methacryloylamino)propyl]trimethylammonium chloride (MAPTAC), or mixture thereof.

In some other embodiments, the activated olefin is 2-(acryloyloxy)-N,N,N-trimethylethanaminium chloride (DMAEA-MCQ), N,N-dimethylaminoethyl acrylate benzyl chloride quaternary salt (DMAEA-BCQ), 2-(methacryloyloxy)-N,N,N-trimethylethan-1-aminium methyl sulfate (DMAEA-MSQ), 2-(acryloyloxy)-N,N,N-trimethylethanaminium chloride (DMAEA-MSQ), or mixture thereof.

In In some embodiments, the compound is derived from a primary amine and an activated olefin. In some embodiments, the activated olefin is acrylic acid, methacrylic acid, itaconic acid, maleic acid, vinylsulfonic acid, vinylphosphonic acid, or mixture thereof.

In some other embodiments, the activated olefin is 2-acrylamido-2-methylpropane sulfonic acid (AMPS), 3-(allyloxy)-2-hydroxypropane-1-sulfonate, or mixture thereof.

In yet some other embodiments, when the activated olefin contains anionic group that can bear negative charge at an alkaline pH, the counter positive ions for the negative charges include, but are not limited to, alkali metal ions, Li$^+$, Na$^+$, K$^+$, NH$_4^+$, a quaternary ammonium ion, etc.

In some embodiments, the compound is soluble or dispersible in water or the corrosion control composition.

In some embodiments, the corrosion control composition comprises a carrier, wherein the carrier is water, an organic solvent, or a mixture thereof.

In some embodiments, the corrosion control composition further comprises an organic solvent. In some other embodiments, the corrosion control composition further comprises an organic solvent and water.

In some embodiments, the organic solvent is an alcohol, a hydrocarbon, a ketone, an ether, an alkylene glycol, a glycol ether, an amide, a nitrile, a sulfoxide, an ester, or any combination thereof. In some other embodiments, the organic solvent is an alcohol, an alkylene glycol, an alkyleneglycol alkyl ether, or a combination thereof. In yet some embodiments, the organic solvent is methanol, ethanol, propanol, isopropanol, butanol, isobutanol, monoethyleneglycol, ethyleneglycol monobutyl ether, or a combination thereof.

In some embodiments, the organic solvent is methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, a mixture thereof with water, or any combination thereof.

In some embodiments, wherein the corrosion control composition further comprises one or more of additional corrosion inhibitors. In some embodiments, wherein the corrosion control composition further comprises one or more of additional corrosion inhibitors and a carrier. In some embodiments, the corrosion inhibitor is an imidazoline compound, a pyridinium compound, or a combination thereof.

In some embodiments, the corrosion control composition further comprises a fouling control agent. In some embodiments, the fouling control agent is a single quat compound.

In some embodiments, the corrosion control composition further comprises a biocide. In some embodiments, the corrosion control composition further comprises a biocide and carrier. In some other embodiments, the corrosion control composition further comprises a biocide, corrosion inhibitor, and carrier.

In some embodiments, the biocide is an oxidizing biocide. In some other embodiments, the biocide is a non-oxidizing biocide. In some other embodiments, the biocide is chlorine, hypochlorite, $ClO_2$, bromine, ozone, hydrogen peroxide, peracetic acid, peroxysulphate, peroxycarboxylic acid, peroxycarboxylic acid composition, or mixture thereof. In some other embodiments, the biocide is glutaraldehyde, dibromonitrilopropionamide, isothiazolone, terbutylazine, polymeric biguanide, methylene bisthiocyanate, tetrakis hydroxymethyl phosphonium sulphate, and combination thereof.

In some embodiments, the corrosion control composition further comprises an organic sulfur compound. In some other embodiments, wherein the organic sulfur compound is a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof.

In some embodiments, the corrosion control composition further comprises an acid. In some embodiments, the corrosion control composition further comprises an inorganic acid, mineral acid, organic acid, or mixture thereof. In some embodiments, the corrosion control composition comprises from about 1 wt-% to about 20 wt-% of the acid.

In some embodiments, the acid is hydrochloric acid, hydrofluoric acid, citric acid, formic acid, acetic acid, or mixture thereof.

In some embodiments, the corrosion control composition further comprises a hydrogen sulfide scavenger. In some other embodiments, the hydrogen sulfide scavenger is an oxidant, inorganic peroxide, sodium peroxide, chlorine dioxide; a $C_1$-$C_{10}$ aldehyde, formaldehyde, glyoxal, glutaraldehyde, acrolein, or methacrolein, a triazine, monoethanolamine triazine, monomethylamine triazine, or a mixture thereof.

In some embodiments, the corrosion control composition further comprises a surfactant. In some embodiments, the corrosion control composition further comprises a surfactant, biocide, and carrier.

In some embodiments, the surfactant is a nonionic, semi-nonionic, cationic, anionic, amphoteric, zwitterionic, Gemini, di-cationic, di-anionic surfactant, or mixtures thereof.

In some embodiments, the surfactant is an alkyl phenol, fatty acid, or mixture thereof.

In some embodiments, the corrosion control composition further comprises an asphaltene inhibitor, a paraffin inhibitor, a scale inhibitor, a gas hydrate inhibitor, a pH modifier, or any combination thereof.

In some embodiments, the corrosion control composition further comprises an emulsion breaker, reverse emulsion breaker, coagulant/flocculant agent, a water clarifier, a dispersant, antioxidant, polymer degradation prevention agent, permeability modifier, foaming agent, antifoaming agent, emulsifying agent, scavenger agent for $CO_2$, and/or $O_2$, gelling agent, lubricant, friction reducing agent, salt, or mixture thereof.

In some embodiments, the corrosion control composition is a liquid, gel, or a mixture comprising liquid/gel and solid.

In some embodiments, the corrosion control composition or a use solution thereof has a pH of from about 1 to about 11, from about 1 to about 3, from about 3 to about 5, from about 5 to about 7, from about 7 to about 9, from about 9 to about 11, about 2, about 4, about 6, about 8, about 10, or any value there between.

In some embodiments, the corrosion control composition comprises from about 10 wt-% to about 80 wt-% of a di-cationic compound or mixture thereof. In some other embodiments, the corrosion control composition comprise from about 10 wt-% to about 30 wt-%, from about 30 wt-% to about 50 wt-%, from about 50 wt-% to about 70 wt-%; from about 10 wt-% to about 40 wt-%, from about 20 wt-% to about 50 wt-%; from about 30 wt-% to about 60 wt-%; from about 40 wt-% to about 80 wt-%, about 15 wt-%, about 25 wt-%, about 35 wt-%, about 45 wt-%, about 55 wt-%, about 65 wt-%, about 75 wt-%, or any value there between of a di-cationic compound or mixture thereof.

In some embodiments, the corrosion control composition comprises from about 20 wt-% to about 60 wt-% of a di-anionic compound or mixture thereof. In some other embodiments, the corrosion control composition comprise from about 10 wt-% to about 30 wt-%, from about 30 wt-% to about 50 wt-%, from about 50 wt-% to about 70 wt-%; from about 10 wt-% to about 40 wt-%, from about 20 wt-% to about 50 wt-%; from about 30 wt-% to about 60 wt-%; from about 40 wt-% to about 80 wt-%, about 15 wt-%, about 25 wt-%, about 35 wt-%, about 45 wt-%, about 55 wt-%, about 65 wt-%, about 75 wt-%, or any value there between of a di-anionic compound or mixture thereof.

In some embodiments, the di-cationic or di-anionic compound or mixture thereof has a concentration of from about 1 ppm to about 1000 ppm in the treated water system. In some embodiments, the di-cationic or di-anionic compound or mixture thereof has a concentration of from about 1 ppm to about 5 ppm, from about 5 ppm to about 10 ppm, from about 1 ppm to about 10 ppm, from about 1 ppm to about 20 ppm, from about 1 ppm to about 25 ppm, from about 5 ppm to about 15 ppm, from about 15 ppm to about 50 ppm, from about 50 ppm to about 100 ppm, from about 100 ppm to about 200 ppm, from about 200 ppm to about 300 ppm, from about 300 ppm to about 400 ppm, from about 400 ppm to about 500 ppm, from about 500 ppm to about 600 ppm, from about 600 ppm to about 700 ppm, from about 700 ppm to about 800 ppm, from about 800 ppm to about 900 ppm, or any value there between in the treated water system.

In some embodiments, the corrosion control composition is provided to the water system independently, simultaneously, or sequentially with an additional functional ingredient.

In some embodiments, the water system comprises fresh water, recycled water, salt water, surface water, produced water, or mixture thereof. In some embodiments, the water system comprises water, oil, and solid, as those found in oil and gas operations. In some embodiments, the water system comprises water and hydrocarbon or oil.

In some embodiments, the water system is a cooling water system, boiler water system, petroleum wells, downhole formations, geothermal wells, mineral washing, flotation and benefaction, papermaking, gas scrubbers, air washers, continuous casting processes in the metallurgical industry, air conditioning and refrigeration, water reclamation, water purification, membrane filtration, food processing, clarifiers, municipal sewage treatment, municipal water treatment, or potable water system.

In some embodiments, the corrosion control composition or di-cationic or di-anionic compounds disclosed herein can prevent corrosion on a surface in a water system as indicated by a bubble cell test described in the Examples section of this disclosure, when the treated water system has a di-cationic or di-anionic concentration of from about 1 ppm to about 1,000 ppm, from about 1 to about 900 ppm, from about 1 ppm to about 800 ppm, from about 1 ppm to about 700 ppm, from about 1 ppm to about 600 ppm, from about 1 ppm to about 500 ppm, from about 1 ppm to about 400 ppm, from about 1 ppm to about 300 ppm, from about 1 ppm to about 250 ppm, from about 1 ppm to about 200 ppm, from about 1 ppm to about 150 ppm, from about 1 ppm to about 100 ppm, from about 1 ppm to about 50 ppm, from about 1 ppm to about 25 ppm, from about 1 ppm to about 10 ppm, from about 0.5 ppm to about 2 ppm, about 950 ppm, about 850 ppm, about 750 ppm, about 650 ppm, about 550 ppm, about 450 ppm, about 350, about 250 ppm, about 150 ppm, about 50 ppm, about 25 ppm, about 10 ppm, about 5 ppm, about 2 ppm, about 1 ppm, about 0.5 ppm, or any range or value there between, after dosing the water system with the di-cationic or di-anionic, or the corrosion control composition.

As used herein, the term "substantially free", "free" or "free of" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present disclosure may comprise, consist essentially of, or consist of the components and ingredients of the disclosed compositions or methods as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Figure 1B:
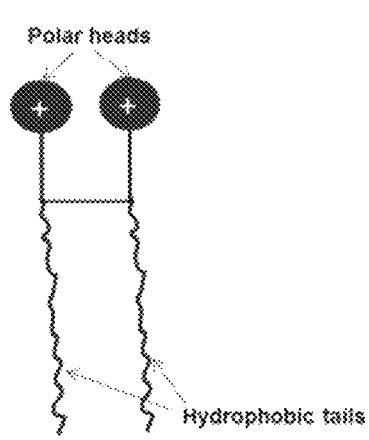
Figure 1C:
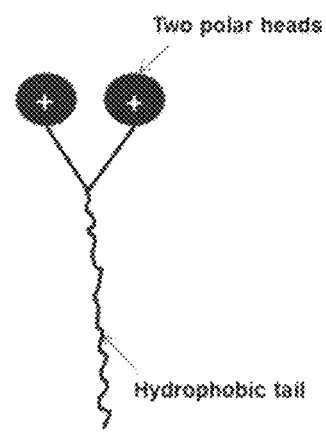

Without being limited to a particular mechanism of action or definition of structure and function of the compounds, the compounds disclosed herein have two hydrophilic groups associated with one hydrophobic group. Accordingly, the compounds disclosed herein have a ratio of hydrophilic heads to hydrophobic tail of 2:1 as compared to both a conventional surfactant and Gemini surfactant, which exhibit a 1:1 ratio. FIG. 1A, FIG. 1B and FIG. 1C show a representation of an exemplary compound disclosed herein (FIG. 1C), together with ones for a conventional (FIG. 1A) and Gemini surfactant (FIG. 1B).

EXAMPLES

Embodiments of the present disclosure are further defined in the following non-limiting Examples. These Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions.

Thus, various modifications of the embodiments of the disclosure, in addition to those shown and described herein, will be apparent to those skilled in the art from the foregoing description. Such modifications are also intended to fall within the scope of the appended claims.

The following non-limiting examples are provided to further illustrate various aspects of the present disclosure. All chemicals were used as received from the supplier unless otherwise noted.

NMR samples of the di-cationic compounds or salts thereof were prepared in $D_2O$. All spectra were acquired at 25° C. Quantitative proton ($^1H$) and carbon ($^{13}C$) were acquired using a single-pulse sequence implemented on an AGILENT 500 MHz spectrometer equipped with a 10 mm broad-band probe for carbon or a 5 mm two-channel probe for proton with Z-gradient. $^1H$ spectra were acquired with 4-8 scans. $^{13}C$ spectra were acquired with 400-500 scans. Data were processed and analyzed using MestReNova v. 9 (Mestrelab, Spain).

The chemical shifts (ppm) are reported relative to TMS (tetramethylsilane) using the residual solvent peak as reference unless otherwise noted. The following abbreviations are used to express the multiplicities: s=singlet; d=doublet; t=triplet; q=quartet; m=multiplet; br=broad.

Mass spectroscopy of the di-cationic compound(s) was conducted on a Q EXACTIVE ORBITRAP high resolution mass spectrometer (Thermo Fisher Scientific) equipped with a quadrupole as an ion filter and with an electrospray ionization (ESI) source. The di-cationic compound samples were diluted to about 100 ppm and then injected into the mass spectrometer by infusion at the flow rate of 10 µL/minute. Spectra were acquired in positive ESI mode; scan range: 50-750 m/z; resolution: 140 k; AGC target: 36; sheath gas flow rate: 2 (arbitrary unit); auxiliary gas flow rate: 0 (arbitrary unit); spray voltage: 2.5 kV; capillary temperature: 150° C.; auxiliary gas heater temperature: 30° C.; and S-Len RF level: 50. Data were acquired and analyzed by XCALIBUR and FREESTYLE software (Thermo Fisher Scientific).

Example 1

General Scheme to Synthesize Exemplary Compounds Containing Two Quaternary Groups:

Exemplary di-cationic compounds containing two quat groups as disclosed herein and in Example Section were synthesized, by aza Michael addition reaction between a primary amine (1 mole) and α,β-unsaturated carbonyl compound containing at least one quat group (at least 2 moles). The generic synthesis reaction scheme for preparation of the di-cationic compounds disclosed herein is shown in FIG. 2.

Figure 2:
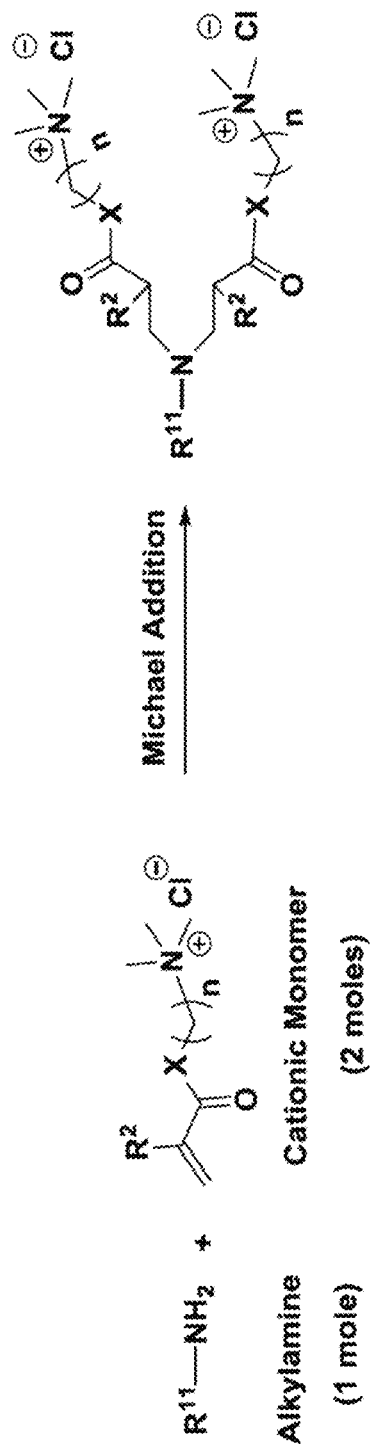
FIG. 2 shows a generic reaction scheme between a primary amine and activated olefin (α, β-unsaturated carbonyl compound) including a cationic group.

In FIG. 2, $R^{11}$ is $R^1$ or $R^1$—Z—$(CH_2)_m$—; $R^1$ is an unsubstituted or substituted, linear or branched $C_5$-$C_{30}$ alkyl, cyclic alkyl, alkenyl, or alkynyl group; Z is NH or O; $R^2$ is H, $CH_3$, or an unsubstituted, linear or branched $C_2$-$C_{10}$ alkyl, alkenyl, or alkynyl group; m is an integer of 1 to 4; and n is an integer of 1-20.

The reaction shown in FIG. 2 can be carried out in water at 80° C. The progression of this reaction can be monitored by ESI-MS and/or NMR spectroscopy for consumption of the monomer. The reaction can be stopped at time when a yield of about 98% for the diquat product had obtained. For reactions that proceeded to completion, the formed product can be separated by removal of solvent or by precipitation in a non-polar solvent that was the opposite of the reaction media. For the reactions in water, the formed product is precipitated from the aqueous reaction mixture. Higher pressure can speed-up the reaction. The compounds I-VI in the following Examples were made according to this generic scheme, but using different reactants as set forth in further detailed in each Example.

Example 2

Synthesis of 3,3'-((3,3'-(octylazanediyl)bis(propanoyl))bis(azanediyl))bis(N,N,N-trimethylpropan-1-aminium) chloride (I)

In this Example, (3-acrylamidopropyl) trimethylammonium chloride (APTAC, 75%, 30 grams, 0.10 mol) was charged into a 250-mL three-necked round bottom flask (RBF) equipped with an overhead stirrer, temperature probe, and condenser. Benzyltrimethylammonium hydroxide (0.9 grams, 10%, 0.0005 mol) and water (41 g) were added into the flask. Octylamine (7 grams, 99%, 0.053 mol) was then added portion wise to the well-stirred reaction mixture. The resulting suspension was stirred at 80° C. overnight. As the reaction proceeded to completion, the suspension turned into a clear yellowish solution. The resulting (~37 wt %) aqueous solution of the diquat compound was stored in the container. Mass spectrometry (+ESI-MS) confirmed synthesis of the diquat compound I: calc. $[M-2Cl^-]^{2+}$ 235.73, found 235.7241; calc. $[M-Cl^-]^+$ 506.42, found 506.4182.

Example 3

Synthesis of 3,3'-((3,3'-(dodecylazanedyl) bis(propanoyl))bis(azanediyl))bis(N,N,N-trimethylpropan-1-aminium) chloride (II)

In this example, (3-acrylamidopropyl) trimethylammonium chloride (APTAC, 75%, 30 grams, 0.10 mol) was charged into a 250-mL three-necked RBF equipped with an overhead stirrer, temperature probe, and condenser. Benzyltrimethylammonium hydroxide (0.9 grams, 10%, 0.0005 mol) and water (63 g) were added into the flask. Dodecylamine (10 grams, 98%, 0.053 mol) was then added portion wise to the well-stirred reaction mixture. The resulting suspension was stirred at 80° C. overnight. As the reaction proceeded to completion, the suspension turned into a clear yellowish solution. The resulting (~31 wt %) aqueous solution of the diquat compound II was used as is. Mass spectrometry (+ESI-MS) confirmed synthesis of diquat compound II: calc. $[M-2Cl^-]^{2+}$ 263.76, found 263.7554; calc. $[M-Cl^-]^+$ 562.48, found 562.4806.

Example 4

Synthesis of 3,3'-((3,3'-(hexadecylazanediyl)bis(propanoyl))bis(azanediyl))bis(N,N,N-trimethylpropan-1-aminium) chloride (III)

In this example, (3-acrylamidopropyl) trimethylammonium chloride (APTAC, 75%, 41 grams, 0.149 mol) was charged into a 250-mL three-necked RBF equipped with an overhead stirrer, temperature probe, and condenser. Benzyltrimethylammonium hydroxide (0.9 grams, 10%, 0.0005 mol) and water (100 g) were added into the flask. Hexadecylamine (20 grams, 90%, 0.0745 mol) was then added portion wise to the well-stirred reaction mixture. The resulting suspension was stirred at 80° C. overnight. As the reaction proceeded to completion, the suspension turned into a clear yellowish solution. The resulting (~30 wt %) aqueous solution of the diquat compound III was used as is. Mass spectrometry (+ESI/MS) confirmed synthesis of diquat compound III: calc. $[M-2Cl^-]^{2+}$ 291.79, found 291.7870; calc. $[M-Cl^-]^+$ 618.54, found 618.5439.

Example 5

Synthesis of 3,3'-((3,3'-(octylazanediyl)bis(propanoyl))bis(azanediyl))bis(N,N,N-trimethylpropan-1-aminium) chloride (IV)

In this example, (3-acrylamidopropyl) trimethylammonium chloride (APTAC, 75%, 40 grams, 0.145 mol) was charged into a 250-mL three-necked RBF equipped with an overhead stirrer, temperature probe, and condenser. Benzyltrimethylammonium hydroxide (0.9 grams, 10%, 0.0005 mol) and water (100 g) were added into the flask. Octadecylamine (20 grams, 98%, 0.072 mol) was then added portion wise to the well-stirred reaction mixture. The resulting suspension was stirred at 80° C. overnight. As the reaction proceeded to completion, the suspension turned into a clear yellowish solution. The resulting (~31 wt %) aqueous solution of the diquat compound IV was used as is. Mass spectrometry (+ESI-MS) confirmed synthesis of the diquat compound IV: calc. $[M-2Cl^-]^{2+}$ 305.80, found 305.8014; calc. $[M-Cl^-]^+$ 646.58, found 648.5791.

Example 6

Synthesis of 3,3'-((3,3'-(octadec-9-en-1-ylazanediyl) bis(propanoyl)) bis(azanediyl)) bis(N,N,N-trimethylpropan-1-aminium) chloride (V)

In this example, (3-acrylamidopropyl) trimethylammonium chloride (APTAC, 75%, 30 grams, 0.109 mol) was charged into a 250-mL three-necked RBF equipped with an overhead stirrer, temperature probe, and condenser. Benzyltrimethylammonium hydroxide (0.25 grams, 10%, 0.0001 mol) and water (70 g) were added into the flask. Oleylamine (15 grams, 95%, 0.053 mol) was then added portion wise to the well-stirred reaction mixture. The resulting suspension was stirred at 80° C. overnight. As the reaction proceeded to completion, the suspension turned into a clear yellowish solution. The resulting (~32 wt %) aqueous solution of the diquat compound V was used as is. Mass spectrometry (+ESI-MS) confirmed synthesis of the diquat compound V: calc. $[M-2Cl^-]^{2+}$ 304.80, found 304.7949; calc. $[M-Cl^-]^+$ 644.56, found 644.5596.

Example 7

Synthesis of 3,3'-((3,3'-((3-(octadec-9-en-1-ylamino)propyl)azanediyl)bis(propanoyl))bis(azanediyl)) bis(N,N,N-trimethylpropan-1-aminium) chloride (VI)

In this example, (3-acrylamidopropyl) trimethylammonium chloride (APTAC, 75%, 42 grams, 0.152 mol) was charged into a 250-mL three-necked RBF equipped with an overhead stirrer, temperature probe, and condenser. Benzyltrimethylammonium hydroxide (0.25 grams, 10%, 0.0001 mol) and water (130 g) were added into the flask. N-oleylpropanediamine (25 grams, 99%, 0.076 mol) was then added portion wise to the well-stirred reaction mixture. The resulting suspension was stirred at 80° C. overnight. As the reaction proceeded to completion, the suspension turned into a clear yellowish solution. The resulting (~28 wt %) aqueous solution of the diquat compound VI was used as is. Mass spectrometry (+ESI/MS) confirmed synthesis of diquat compound VI: calc. $[M-2Cl^-]^{2+}$ 333.32, found 333.3238; calc. $[M-Cl^-]^+$ 701.62, found 701.6173.

Example 8

Corrosion Control Efficacy of Some Exemplary Di-Cationic Compounds

In this Example, some exemplary di-cationic compounds were tested for their efficacy to prevent corrosion. The tested samples were made according to the reaction presented in Example 1 and listed in the following Table 2. The precursor primary amine for each compound is listed and the other reactant to produce the listed samples is (3-acrylamidopropyl) trimethylammonium chloride.

TABLE 2

List of the exemplary compounds for corrosion control test.

| Sample ID: | Chemistry AMINE (R—NH$_2$) |
|---|---|
| 1 | HEXADECYLAMINE |
| 2 | OCTADECYLAMINE |
| 3 | OLEYLAMINE |
| 4 | N-OLEYLPROPANEDIAMINE |
| 5 | OCTYLAMINE |
| 6 | DODECYLAMINE |
| 7 | CORSAMINE DT |
| 8 | CORSAMINE TRT |

The efficacy for corrosion control is usually measured by corrosion bubble cell tests. The bubble test simulates low flow areas where little or no mixing of water and oil occurs. The test was conducted in fluids containing 80% brine (3% sodium chloride) and 20% hydrocarbon (75% LVT-200 and 25% xylene). The fluids were placed into kettles and purged with carbon dioxide. The brine was placed into kettles and purged with carbon dioxide. The brine was continually purged with carbon dioxide to saturate the brine prior to starting the test. After the test began, the test cell was blanketed with carbon dioxide one hour prior to electrode insertion and through the duration of the test to maintain saturation. The kettles were stirred at 150 revolutions per minute (rpm) for the duration of the test to maintain thermal equilibrium at 80° C. The corrosion rate was measured by Linear Polarization Resistance (LPR) techniques. The working electrode used was 1018 carbon steel. The counter and reference electrodes were both Hastelloy. The electrodes were all cleaned and polished prior to testing. Data were collected for three hours before 20 ppm of each of the compositions (containing 2 ppm of each of various di-cationic compounds or salts thereof or the control $C_{12}$-$C_{18}$ alkyl dimethyl benzyl ammonium chloride and 1% 2-mercaptoethanol (2ME) as synergist in an organic solvent) was dosed into its respective cell. Data were collected overnight.

The control compounds for this Example are commonly used benzyl ammonium chloride quaternary chemistry and imidazoline chemistry, respectively.

Figure 3:
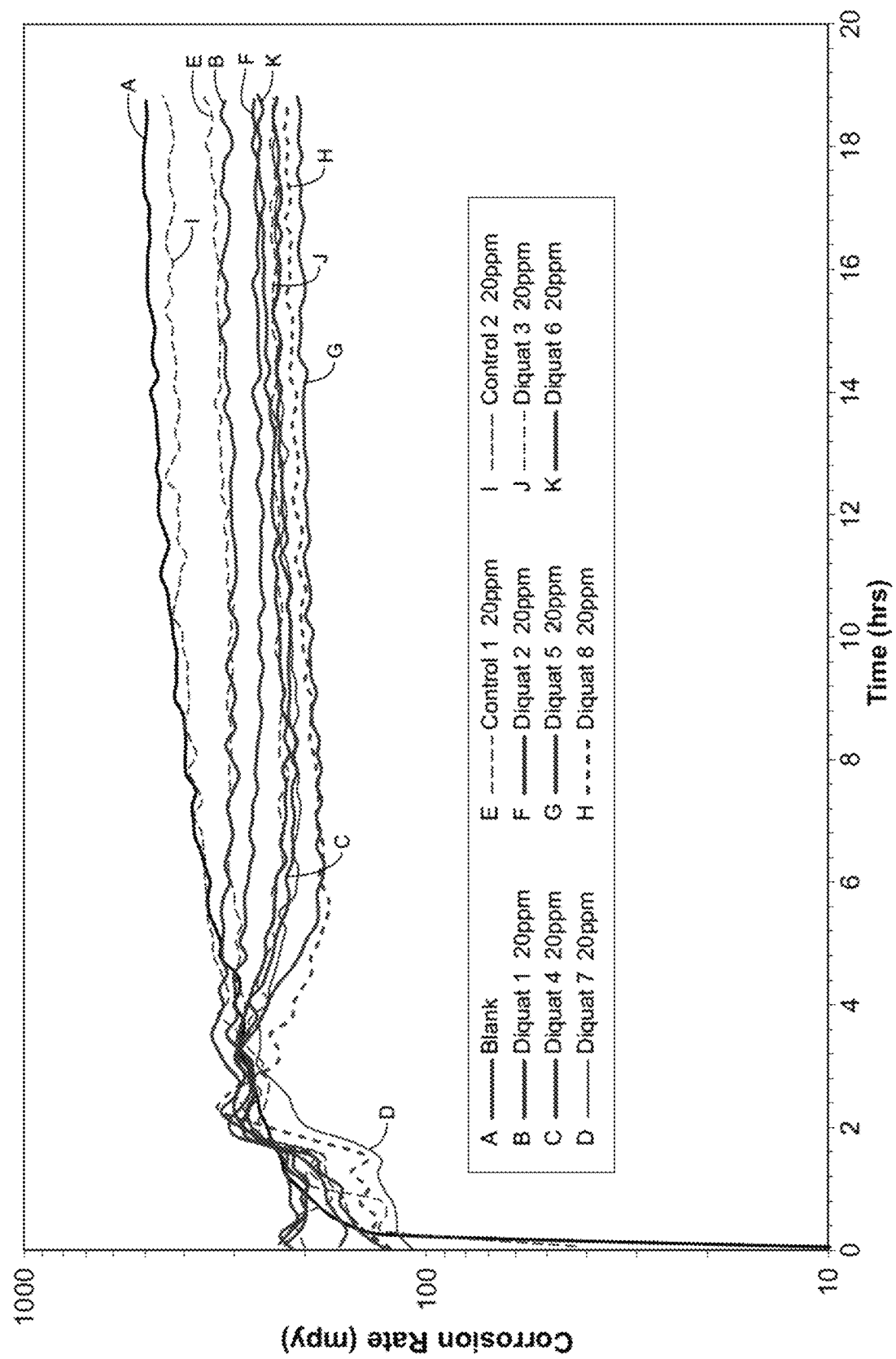
FIG. 3 shows the corrosion rate in mils per year (mpy) during the bubble test period (18 hour). For the blank sample, no 2-mercaptoethanol (2ME) was added.

The results of the bubble test are shown in FIG. 3 and Table 3, wherein ppm is parts per million, CI is corrosion inhibitor, and mpy is mils per year. 0.2 ppm of 2-mercaptoethanol (2ME) were present with each tested di-cationic compound or control. FIG. 3 shows the corrosion rate in mils per year during the bubble test period (18 hour). For the blank sample, no 2-mercaptoethanol (2ME) was added.

TABLE 3

Corrosion rate at 15th Hour after Di-cationic compound or control compound addition in bubble test results

| Di-cationic Salt or Control Cationic Compound | Dosage of Cationic Polymer Salt or Compound (ppm) | Inhibited Corrosion Rate 15 h After Di-cationic Salt or Control Addition (mpy) | % Protection |
|---|---|---|---|
| Blank | 0 | 500 | −92 |
| $C_{12}$-$C_{18}$ alkyl dimethyl benzyl ammonium chloride (Control 1) | 2 | 339 | 32 |
| TOFA:DETA imidazoline salted with acetic acid (Control 2) | 2 | 432 | 14 |
| 1 | 2 | 235 | 53 |
| 2 | 2 | 264 | 47 |
| 3 | 2 | 239 | 52 |
| 4 | 2 | 232 | 54 |
| 5 | 2 | 206 | 59 |
| 6 | 2 | 258 | 48 |
| 7 | 2 | 318 | 36 |
| 8 | 2 | 220 | 88 |

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A method of for inhibiting corrosion at a surface in a water system comprising:

providing a corrosion control composition or a use solution of the corrosion control composition into a water system to generate a treated water system or onto to a surface of the water system, wherein the corrosion control composition comprises one or more compounds according to one of Formula I, Formula II, Formula III and one or more additional corrosion control composition agents,

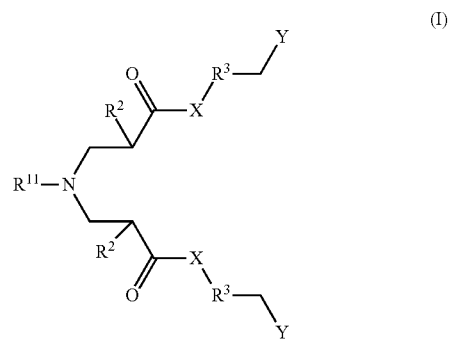

-continued

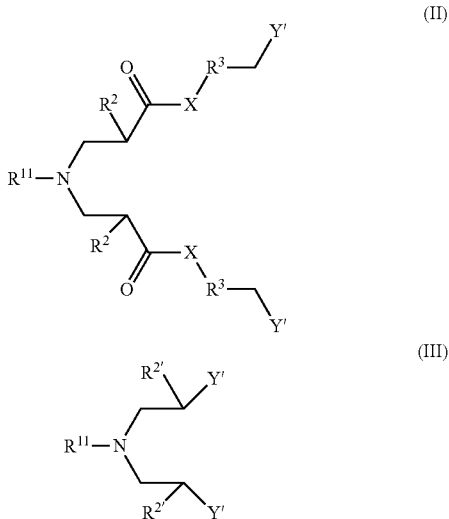

wherein:
X is NH or O;
$R^{11}$ is $R^1$ or $R^1$—Z—$(CH_2)_m$—;
$R^1$ is an unsubstituted or substituted, linear or branched $C_5$-$C_{30}$ alkyl, cyclic alkyl, alkenyl, or alkynyl group;
Z is NH or O;
$R^2$ is H, $CH_3$, or an unsubstituted, linear or branched $C_2$-$C_{10}$ alkyl, alkenyl, or alkynyl group;
m is an integer of 1 to 4;
$R^3$ is absent or an unsubstituted, linear $C_1$-$C_{30}$ alkylene group;
Y is —$NR_4R_5R_6^{(+)}$;
Y' is —COOH, —$SO_3H$, —$PO_3H$, —$OSO_3H$, —$OPO_3H$, or a salt thereof; and
$R^4$, $R^5$, and $R^6$ are independently a $C_1$-$C_{10}$ alkyl group;
$R^{2'}$ is H, $CH_3$, or an unsubstituted or substituted, linear or branched $C_1$-$C_{10}$ alkyl, alkenyl, alkynyl group, —COOH, —$CH_2COOH$, Y', or —$(CH_2)_m$—Y' and
wherein the corrosion control composition mitigates corrosion on the surface in the water system.

2. The method according to claim 1, wherein X is NH.

3. The method according to claim 1, wherein X is O.

4. The method according to claim 1, wherein $R^{11}$ is $R^1$ and $R^1$ is a linear $C_5$-$C_{30}$ alkyl, alkenyl, or alkynyl group.

5. The method according to claim 1, wherein $R^{11}$ is $R^1$—Z—$(CH_2)_m$— or $R^1$—Z—$(CH_2)_2$—, Z is NH, and $R^1$ is a linear $C_5$-$C_{30}$ alkyl, alkenyl, or alkynyl group.

6. The method according to claim 1, wherein $R^{11}$ is $R^1$—Z—$(CH_2)_m$—, Z is O, and $R^1$ is a linear $C_5$-$C_{30}$ alkyl, alkenyl, or alkynyl group.

7. The method according to claim 1, wherein $R^2$ is H or $CH_3$.

8. The method according to claim 1, wherein Y is —$NR^4R^5R^{6(+)}$, $N(CH_3)_3^+$, $N(CH_3)_2R_6^+$, and wherein $R^6$ is a $C_2$-$C_{12}$ alkyl, aryl, or is —$CH_2$—$C_6H_5$.

9. The method according to claim 1, wherein $R^3$ is $CH_2$, $CH_2CH_2$, or $C(CH_3)_2$, an unsubstituted and linear $C_2$-$C_{10}$ alkylene group.

10. The method according to claim 1, wherein $R^{11}$ is a $C_6$-$C_{20}$ alkenyl group with at least one trans or cis double bond.

11. The method according to claim 1, wherein the corrosion control composition agent is a carrier, wherein the carrier is water, an organic solvent, or a mixture thereof.

12. The method according to claim 1, wherein the corrosion control composition agent is a carrier and one or more additional corrosion inhibitors.

13. The method according to claim 1, wherein the corrosion control composition agent is a biocide, wherein the biocide is chlorine, hypochlorite, $ClO_2$, bromine, ozone, hydrogen peroxide, peracetic acid, peroxycarboxylic acid composition, peroxysulphate, glutaraldehyde, dibromonitrilopropionamide, isothiazolone, terbutylazine, polymeric biguanide, methylene bisthiocyanate, tetrakis hydroxymethyl phosphonium sulphate, or any combination thereof.

14. The method according to claim 1, wherein the corrosion control composition agent is an acid and wherein the corrosion control composition comprises from about 1 wt-% to about 20 wt-% of the acid, wherein the acid is hydrochloric acid, hydrofluoric acid, citric acid, formic acid, acetic acid, or a mixture thereof.

15. The method according to claim 1, wherein the corrosion control composition agent is a surfactant.

16. The method according to claim 1, wherein the corrosion control composition agent is a scale inhibitor, gas hydrate inhibitor, pH modifier, or any combination thereof.

17. The method according to claim 1, wherein the corrosion control composition agent is an emulsion breaker, reverse emulsion breaker, a fouling control agent, coagulant/flocculant agent, an emulsifier, a water clarifier, a dispersant, antioxidant, polymer degradation prevention agent, permeability modifier, foaming agent, antifoaming agent, emulsifying agent, scavenger agent for $CO_2$, and/or $O_2$, gelling agent, lubricant, friction reducing agent, salt, or mixture thereof.

18. The method according to claim 1, wherein the corrosion control composition is a liquid, gel, or a mixture comprising liquid/gel and solid.

19. The method according to claim 1, wherein the corrosion control composition or a use solution thereof has a pH of from about 1 to about 11.

20. The method according to claim 1, wherein the corrosion control composition comprises from about 10 wt-% to about 80 wt-% of the compound.

21. The method according to claim 1, wherein the compound has a concentration of from about 1 ppm to about 1000 ppm in the treated water system.

22. The method according to claim 1, wherein the water system comprises fresh water, recycled water, salt water, surface water, produced water, oil, hydrocarbon, or mixture thereof.

23. The method according to claim 1, wherein the water system is a cooling water system, boiler water system, water system in oil and gas operations, in a petroleum well, downhole formation, geothermal well, mineral washing, flotation and benefaction, papermaking, gas scrubber, air washer, continuous casting processes in the metallurgical industry, air conditioning and refrigeration, water reclamation, water purification, membrane filtration, food processing, clarifiers, municipal sewage treatment, municipal water treatment, or potable water system.

24. A corrosion control composition comprising one or more compounds according to one of Formula I, Formula II, and Formula III and one or more additional corrosion control composition agents,

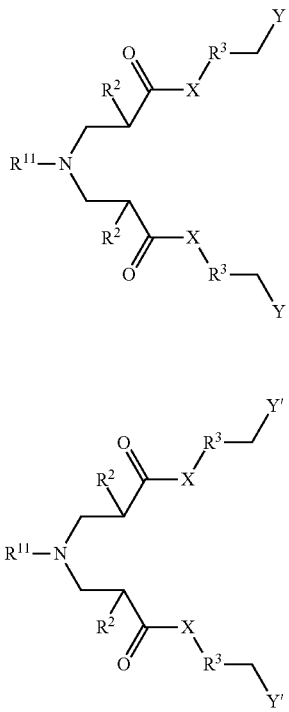

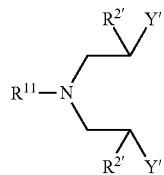

wherein:
X is NH or O;
$R^{11}$ is $R^1$ or $R^1$—Z—$(CH_2)_m$—;
$R^1$ is an unsubstituted or substituted, linear or branched $C_5$-$C_{30}$ alkyl, cyclic alkyl, alkenyl, or alkynyl group;
Z is NH or O;
$R^2$ is H, $CH_3$, or an unsubstituted, linear or branched $C_2$-$C_{10}$ alkyl, alkenyl, or alkynyl group;
m is an integer of 1 to 4;
$R^3$ is absent or an unsubstituted, linear $C_1$-$C_{30}$ alkylene group;
Y is —$NR_4R_5R_6^{(+)}$;
Y' is —COOH, —$SO_3H$, —$PO_3H$, —$OSO_3H$, —$OPO_3H$, or a salt thereof;
$R^4$, $R^5$, and $R^6$ are independently a $C_1$-$C_{10}$ alkyl group;
$R^{2'}$ is H, $CH_3$, or an unsubstituted or substituted, linear or branched $C_1$-$C_{10}$ alkyl, alkenyl, alkynyl group, —COOH, —$CH_2COOH$, Y', or —$(CH_2)_m$—Y', and
wherein the corrosion control composition mitigates corrosion on the surface in the water system.

\* \* \* \* \*

UNITED STATES PATENT AND TRADEMARK OFFICE
CERTIFICATE OF CORRECTION

PATENT NO. : 11,021,383 B2
APPLICATION NO. : 16/116413
DATED : June 1, 2021
INVENTOR(S) : Ashish Dhawan et al.

Page 1 of 1

It is certified that error appears in the above-identified patent and that said Letters Patent is hereby corrected as shown below:

In the Claims

At Column 40, at approximately Line 41, Claim 1:
Delete: "for"

Signed and Sealed this
Twenty-third Day of May, 2023

Katherine Kelly Vidal
*Director of the United States Patent and Trademark Office*